US010271764B2

United States Patent
Sweeney et al.

(10) Patent No.: US 10,271,764 B2
(45) Date of Patent: Apr. 30, 2019

(54) INTRALUMINAL DEVICES WITH DEPLOYABLE ELEMENTS

(71) Applicant: ELWHA LLC, Bellevue, WA (US)

(72) Inventors: Elizabeth A. Sweeney, Seattle, WA (US); Jordin T. Kare, San Jose, CA (US)

(73) Assignee: ELWHA LLC, Bellevue, WA (US)

( * ) Notice: Subject to any disclaimer, the term of this patent is extended or adjusted under 35 U.S.C. 154(b) by 143 days.

(21) Appl. No.: 15/255,708

(22) Filed: Sep. 2, 2016

(65) Prior Publication Data
US 2018/0064366 A1 Mar. 8, 2018

(51) Int. Cl.
| | |
|---|---|
| *A61B 5/06* | (2006.01) |
| *A61B 5/00* | (2006.01) |
| *A61B 17/00* | (2006.01) |
| *A61B 5/07* | (2006.01) |
| A61B 1/04 | (2006.01) |
| A61B 5/01 | (2006.01) |
| A61B 5/03 | (2006.01) |
| A61B 5/145 | (2006.01) |
| A61B 10/02 | (2006.01) |
| A61B 18/00 | (2006.01) |
| A61M 5/142 | (2006.01) |

(52) U.S. Cl.
CPC .............. *A61B 5/068* (2013.01); *A61B 5/073* (2013.01); *A61B 5/6861* (2013.01); *A61B 17/00234* (2013.01); A61B 1/041 (2013.01); A61B 5/01 (2013.01); A61B 5/036 (2013.01); A61B 5/14539 (2013.01); A61B 10/02 (2013.01); A61B 18/00 (2013.01); A61B 2017/00017 (2013.01); A61B 2017/00345 (2013.01); A61B 2560/0219 (2013.01); A61M 5/14276 (2013.01)

(58) Field of Classification Search
CPC ....... A61B 5/068; A61B 5/6861; A61B 5/036; A61B 5/14539; A61B 5/01
USPC .................................................. 600/300, 301
See application file for complete search history.

(56) References Cited

U.S. PATENT DOCUMENTS

| | | |
|---|---|---|
| 6,939,292 B2 | 9/2005 | Mizuno |
| 7,001,329 B2 | 2/2006 | Kobayashi et al. |
| 7,180,265 B2 | 2/2007 | Naskali et al. |
| 7,998,067 B2 | 8/2011 | Kimoto et al. |
| 8,060,214 B2 | 11/2011 | Larson et al. |

(Continued)

FOREIGN PATENT DOCUMENTS

WO 2014193922 12/2014

OTHER PUBLICATIONS

PCT International Search Report; International App. No. PCT/US2017/049294; dated Dec. 13, 2017; pp. 1-6.

(Continued)

*Primary Examiner* — Michael Carey
(74) *Attorney, Agent, or Firm* — Daniel J. Honz; Advent, LLP

(57) ABSTRACT

Intraluminal devices with deployable elements are described. An intraluminal device includes, but is not limited to, a shell dimensioned and structured to travel through a biological lumen of a subject; and at least one deployable element, the at least one deployable element being actuatable from a first configuration to at least a second configuration, wherein the at least one deployable element extends further outwards from the shell in the second configuration than in the first configuration.

15 Claims, 22 Drawing Sheets

(56) References Cited

U.S. PATENT DOCUMENTS

| | | | |
|---|---|---|---|
| 2002/0198439 A1 | 12/2002 | Mizuno | |
| 2004/0054278 A1 | 3/2004 | Kimchy et al. | |
| 2008/0161639 A1* | 7/2008 | Katayama | A61B 1/041 600/104 |
| 2008/0306360 A1 | 12/2008 | Robertson et al. | |
| 2009/0234203 A1* | 9/2009 | Arita | A61B 1/00016 600/302 |
| 2011/0257491 A1* | 10/2011 | Robertson | A61B 5/0031 600/302 |
| 2013/0030261 A1* | 1/2013 | Mintchev | A61B 1/00158 600/302 |
| 2016/0038086 A1 | 2/2016 | Wrigglesworth et al. | |

OTHER PUBLICATIONS

Pan, Guobing; Wang, Litong; "Swallowable Wireless Capsule Endoscopy: Progress and Technical Challenges", vol. 2012, Article ID 841691, 9 pp., Oct. 10, 2011, Gastroenterology Research and Practice.

Basar, MD Rubel; Ahmad, Mohd Yazed; Cho, Jongman; Ibrahim, Fatimah; "Application of Wireless Power Transmission Systems in Wireless Capsule Endoscopy: An Overview", pp. 10929-10951, Jun. 19, 2014, Sensors 2014, 14.

Lazzi, Gianluca; "Thermal Effects of Bioimplants", pp. 75-81, Sep.-Oct. 2005, IEEE Engineering in Medicine and Biology Magazine.

Carta, R.; Sfakiotakis, M.; Pateromichelakis, N.; Thone, J.; Tsakiris, D.P.; Puers, R.; "A Multi-Coil Inductive Powering System for an Endoscopic Capsule with Vibratory Actuation", 2011, Science Direct.

Adeeb, M.A.; Islam, A.B.; Haider, M.R.; Tulip, F.S.; Ericson, M.N.; Islam, S.K.; "An Inductive Link-Based Wireless Power Transfer System for Biomedical Applications", vol. 2012, Article ID 879294, 11 pp., Mar. 5, 2012, Active and Passive Electronic Components.

Andra, W.; d'Ambly, C.G.; Hergt, R.; Hilger, I.; Kaiser, W.A.; "Temperature distribution as function of time around a small spherical heat source of local magnetic hyperthermia", pp. 197-203, Journal of Magnetism and Magnetic Materials 194 (1999).

Cheng, X,; Rahimi, A.; Senior, D.E.; Wu, J.; Yoon, Y.K.; "A dual-function helix antenna with wireless communication and power transmission capabilities for capsule endoscope", pp. 516-519, PowerMEMS 2012.

Liu, Daniel Kuang-Chen; Friend, James; Yeo, Leslie; "A brief review of actuation at the micro-scale using electronics, electromagnetics and piezoelectric ultrasonics", pp. 115-123, The Acoustical Society of Japan 2010.

Olivo, Jacopo; Ghoreishizadeh, Sara S.; Carrara, Sandro; Giovanni, Micheli De; "Electronic Implants: Power Delivery and Management", Integrated Systems Laboratory—EPFL, Mar. 2013, pp. 1540-1545.

* cited by examiner

INTRALUMINAL DEVICES WITH DEPLOYABLE ELEMENTS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, an intraluminal device includes, but is not limited to, a shell dimensioned and structured to travel through a biological lumen of a subject; and at least one deployable element, the at least one deployable element being actuatable from a first configuration to at least a second configuration, wherein the at least one deployable element extends further outwards from the shell in the second configuration than in the first configuration.

In another aspect, an intraluminal device includes, but is not limited to, a shell dimensioned and structured to travel through a biological lumen of a subject; at least one deployable element, the at least one deployable element being actuatable from a first configuration to at least a second configuration, wherein the at least one deployable element extends further outwards from the shell in the second configuration than in the first configuration; at least one first circuit portion at least partially located within the shell; and at least one second circuit portion at least partially located on or within the at least one deployable element, wherein the at least one first circuit portion is electronically connected with the at least one second circuit portion.

In another aspect, an intraluminal device includes, but is not limited to, a shell dimensioned and structured to travel through a biological lumen of a subject; at least one of a sensor or a therapeutic device at least partially located within the shell; at least one controller electronically connected with the at least one of the sensor or the therapeutic device; at least one energy storage device; and at least one deployable antenna assembly including at least one antenna, the at least one antenna being electronically connected with at least one of the at least one controller or the at least one energy storage device, the at least one deployable antenna assembly being actuatable from a first configuration to at least a second configuration, wherein the at least one deployable antenna assembly extends further outwards from the shell in the second configuration than in the first configuration.

In another aspect, a gastrointestinal device includes, but is not limited to, an orally administrable capsule passable through at least a portion of a gastrointestinal tract of a subject; at least one of a sensor or a therapeutic device at least partially located within the orally administrable capsule; at least one controller electronically connected with the at least one of the sensor or the therapeutic device; at least one energy storage device; and at least one deployable antenna assembly including at least one antenna, the at least one antenna being electronically connected with at least one of the at least one controller or the at least one energy storage device, the at least one deployable antenna assembly being actuatable from a first configuration to at least a second configuration, wherein the at least one deployable antenna assembly extends further outwards from the orally administrable capsule in the second configuration than in the first configuration.

In another aspect, a method includes, but is not limited to, introducing a shell with a deployable element attached to the shell into a lumen of a biological subject; and actuating the deployable element from a first configuration to a second configuration, wherein the deployable element extends further outwards from the shell in the second configuration than in the first configuration.

In another aspect, a method includes, but is not limited to, introducing a shell with a deployable antenna assembly attached to the shell into a lumen of a biological subject; actuating the deployable antenna assembly from a first configuration to at least a second configuration, wherein the deployable antenna assembly extends further outwards from the shell in the second configuration than in the first configuration; and sending or receiving at least one electromagnetic signal with the at least one antenna when the antenna assembly is in the second configuration.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
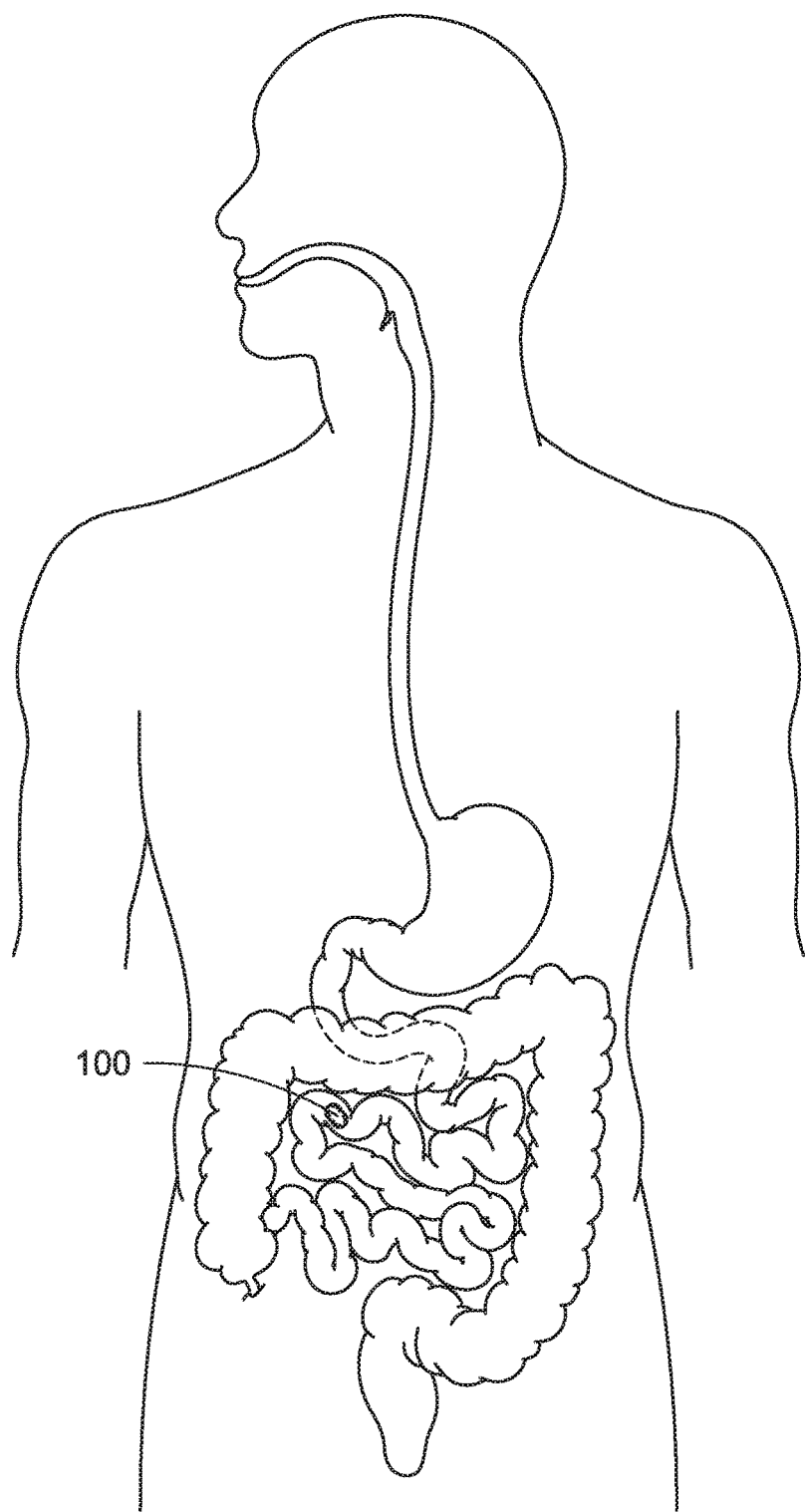
FIG. 1 is a schematic of an intraluminal device with at least one deployable element.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Systems and methods are described for providing intraluminal devices with deployable elements that deploy while placed within an individual subject, such as while an intraluminal device is traveling within one or more biological lumens of the individual subject. The deployable elements can, for example, provide extended antennas, sensor elements, emitter/detector elements, or therapeutic device elements, or antennas, sensor elements, emitter/detector elements, or therapeutic device elements with greater surface area or length, extension to reach luminal walls, or extension of the intraluminal device for enhanced maneuverability. The biological lumens can be associated with any biological lumen network of an individual subject, such as a lumen associated with at least one of a gastrointestinal system, a respiratory system, a cardiovascular system, a nervous system, a urinary system, a reproductive system, a lymphatic system, a biliary system, a glandular system, an auditory system, a visual system, or a nasal system. For example, medical personnel can employ endoscopy techniques to monitor gastrointestinal health, which may lead to the detection of diseases. Endoscopy allows medical personnel to view the tissue comprising the gastrointestinal tract and to more easily identify problems that may otherwise require extensive testing or go undetected. Wired endoscope devices can be utilized for such diagnostics, however such devices often cannot feasibly reach or monitor the small intestine. This leaves medical personnel to speculate about the health of a patient's overall gastrointestinal tract. In some instances, discomfort or pain may be experienced by patients as a wired endoscope is moved through the body, which can cause intestinal perforation. Wireless capsule endoscopy can be utilized to view the entire gastrointestinal tract, while minimizing pain associated with wired endoscopes. Wireless capsule endoscopy uses a capsule that may be small enough for a patient to ingest and may be powered by local power supplies (e.g., batteries).

In some cases, the power supplied from local power supplies may not last long enough for medical personnel to view the entire gastrointestinal tract or to provide other diagnostic or treatment procedures. Intraluminal devices may be inductively charged by sources external to the biological lumen (e.g., external to the gastrointestinal tract of the subject); however, inductive charging can be difficult due to the dimensions or arrangement of components within an intraluminal device. For example, capsule dimensions and form factor may not provide an adequate coil dimensions or antenna extension for receiving energy in the form of a wireless electromagnetic signal from an inductive charger. Wireless communications can be similarly affected, and in some cases, the dimensions and form factor of the intraluminal device can also limit the capability of sensor elements or therapeutic device elements carried by the intraluminal device.

FIGS. 1 through 15 show embodiments of an intraluminal device configured for deployment within one or more biological lumens within an individual subject (e.g., a human subject, an animal subject), such as a lumen of the gastrointestinal tract (as shown in FIG. 1). While FIG. 1 shows the intraluminal device 100 within the lumen of the gastrointestinal tract, the intraluminal device 100 can operate within biological lumens associated with any biological lumen network of an individual subject, such as a lumen associated with at least one of a gastrointestinal system, a respiratory system, a cardiovascular system, a nervous system, a urinary system, a reproductive system, a lymphatic system, a biliary system, a glandular system, an auditory system, a visual system, or a nasal system. For example, embodiments of the intraluminal device 100 described herein may be configured for use in (e.g., configured to fit within) a body lumen of an organism including, for example, the respiratory tract, the cardiovascular system (e.g., a blood vessel), a portion of a CSF-space (cerebro-spinal fluid space) of the nervous system (e.g., the spinal canal, the ventricles of the brain, the sub-arachnoid space, etc.), a portion of the urinary tract (for example a ureter), a portion of the lymphatic system, a portion of the abdominal cavity, a portion of the thoracic cavity, a portion of the digestive tract, a portion of a reproductive tract, either the female reproductive tract (e.g., a lumen of a fallopian tube) or the male reproductive tract (including various lumens including but not limited to the epididymis, vas deferens or ductul deferens, efferent duct, ampulla, seminal duct, ejaculatory duct, or urethra), the biliary tract, a nostril or nasal cavity, the oral cavity, the digestive tract, the tear ducts, or a glandular system. Other body lumens may be found in the auditory or visual system, or in interconnections thereof, e.g., the Eustachian tubes. Some of the systems and devices described herein may be used in a body lumen through which fluid flows, but it is not intended that such devices or systems are limited to use in tubular lumen-containing structures containing moving fluid; in some applications an intraluminal device may be used in a body lumen containing relatively unmoving, or intermittently moving fluid.

As shown in FIGS. 2A through 3E, the intraluminal device 100 includes a shell 102 that defines a body for the intraluminal device 100 and at least one deployable element 104 directly or indirectly attached to the shell 102. For example, the deployable element 104 can be directly coupled with a portion of the shell 102 (e.g., mounted on an inner or outer wall of the shell 102), or the deployable element 104 can be coupled with a component that is carried by the shell 102 (e.g., coupled to an anchoring structure for supporting the deployable element 104, or coupled to an actuator for deploying the deployable element 104). The intraluminal device 100 is generally configured for diagnostic and treatment functionalities within the biological lumen, where the shell 102 facilitates lumen travel by being dimensioned and structured to travel through the biological lumen. For example, the shell 102 can adopt a capsule/structure or a pill shape/structure, or another shape or structure, to facilitate travel through the biological lumen. In embodiments, the shell 102 includes a hermetic seal to protect one or more components of the intraluminal device 100 from the environment within the individual subject. In embodiments, at least a portion of the intraluminal device 100 comprises one or more of a biocompatible material, a biodegradable material, or a bioresorbable or bioabsorbable material (e.g., a natural or synthetic biodegradable or bioresorbable polymer, a bioresorbable ceramic or metal, silk, or paper). For example, at least a portion of the shell 102 can include one or more of a nontoxic material, a biocompatible material, a biodegradable material or a bioresorbable material. The deployable element 104 can also include one or more of a nontoxic material, biocompatible material, a biodegradable material, or a bioresorbable or bioabsorbable material.

Figure 3A:
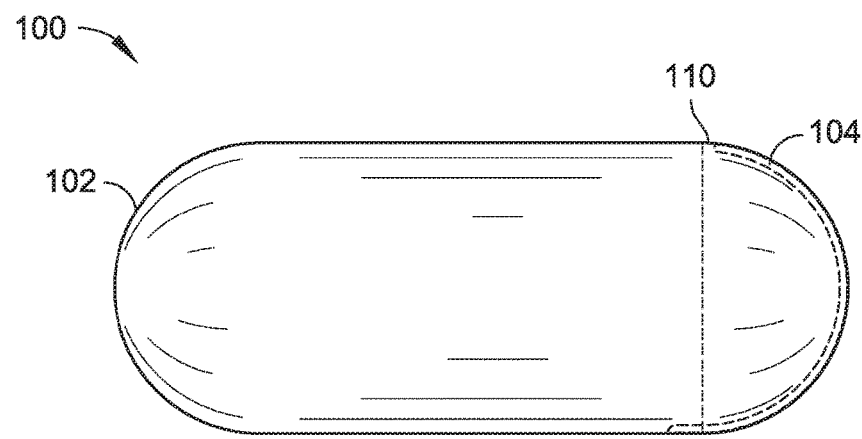
FIG. 3A is a schematic of an embodiment of an intraluminal device such as shown in FIG. 1.
Figure 3B:
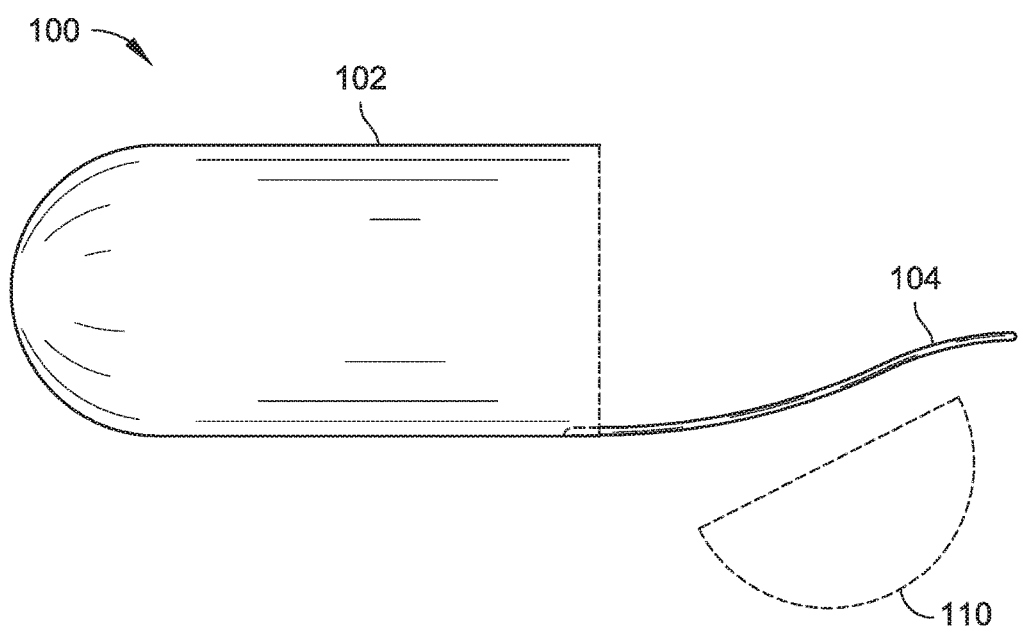
FIG. 3B is a schematic of an embodiment of an intraluminal device such as shown in FIG. 1.
Figure 3C:
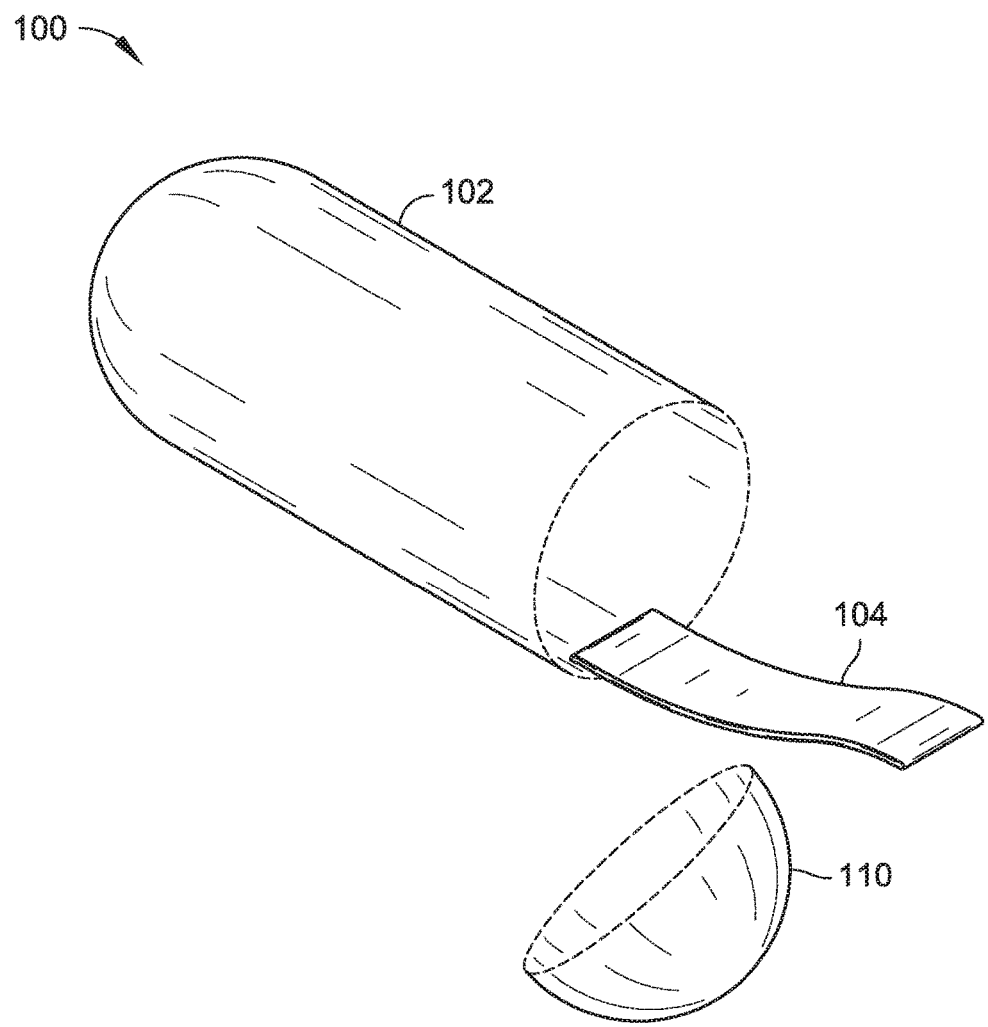
FIG. 3C is a schematic of an embodiment of an intraluminal device such as shown in FIG. 1.

The deployable element 104 is actuatable from a first configuration to at least a second configuration, where the deployable element 104 extends further outwards from the shell 102 in the second configuration than in the first configuration. For example, FIGS. 2A through 2E show an example of the deployable element 104 actuated from a first configuration to a second configuration. FIGS. 3A through 3C shows the deployable element 104 actuated from a first configuration to a second configuration in accordance with another embodiment. In embodiments (e.g., as shown in FIGS. 2A through 2E), the deployable element 104 is at least partially or completely located outside the shell 102 when in the first configuration (e.g., prior to be deployed). For example, the deployable element 104 at least partially unwraps or unfolds from around an outer portion of the shell 102 when it is deployed (e.g., when actuated from the first configuration to the second configuration). In embodiments (e.g., as shown in FIGS. 3A through 3C), the deployable element 104 is at least partially or completely located inside the shell 102 when in the first configuration (e.g., prior to be deployed). For example, the deployable element 104 is released or extended from a storage compartment or cavity defined by the shell 102 when it is deployed (e.g., when actuated from the first configuration to the second configuration). In embodiments, the deployable element 104 is deployed (e.g., extended or released) through an opening in the shell 102. In embodiments, the shell 102 can include a removable portion 110 (e.g., a cap) that at least partially releases or breaks away from the rest of the shell 102 to facilitate deployment of the deployable element 104 (e.g., as shown in FIGS. 3B and 3C).

Figure 2A:
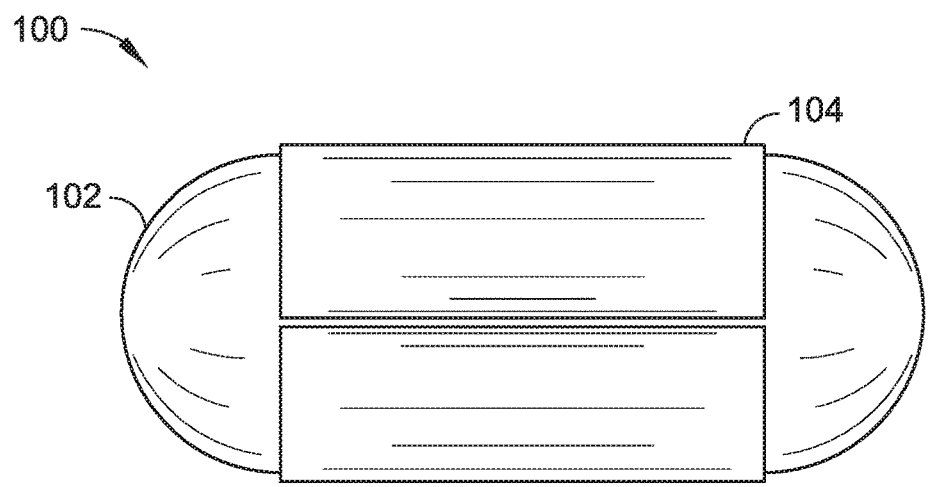
FIG. 2A is a schematic of an embodiment of an intraluminal device such as shown in FIG. 1.
Figure 2B:
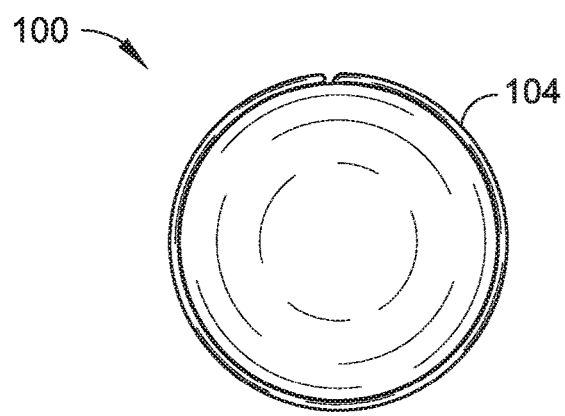
FIG. 2B is a schematic of an embodiment of an intraluminal device such as shown in FIG. 1.
Figure 2C:
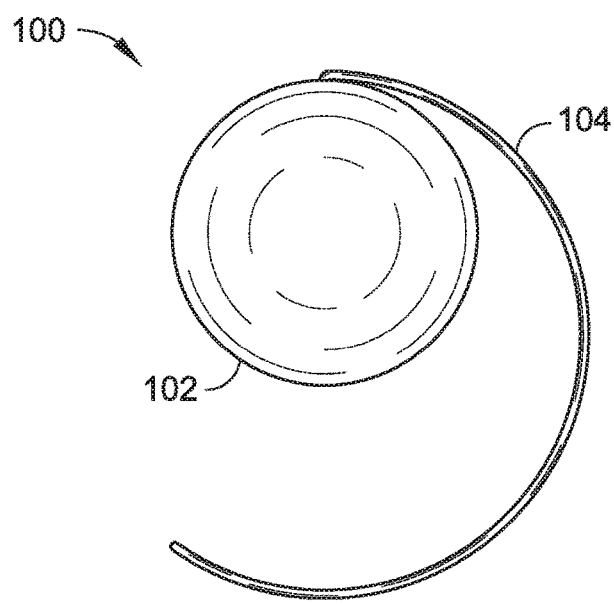
FIG. 2C is a schematic of an embodiment of an intraluminal device such as shown in FIG. 1.
Figure 2D:
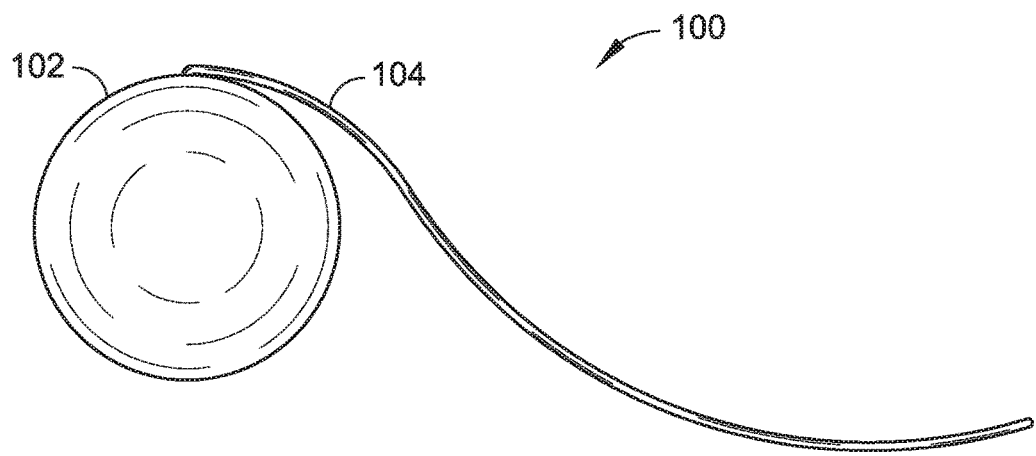
FIG. 2D is a schematic of an embodiment of an intraluminal device such as shown in FIG. 1.
Figure 2E:
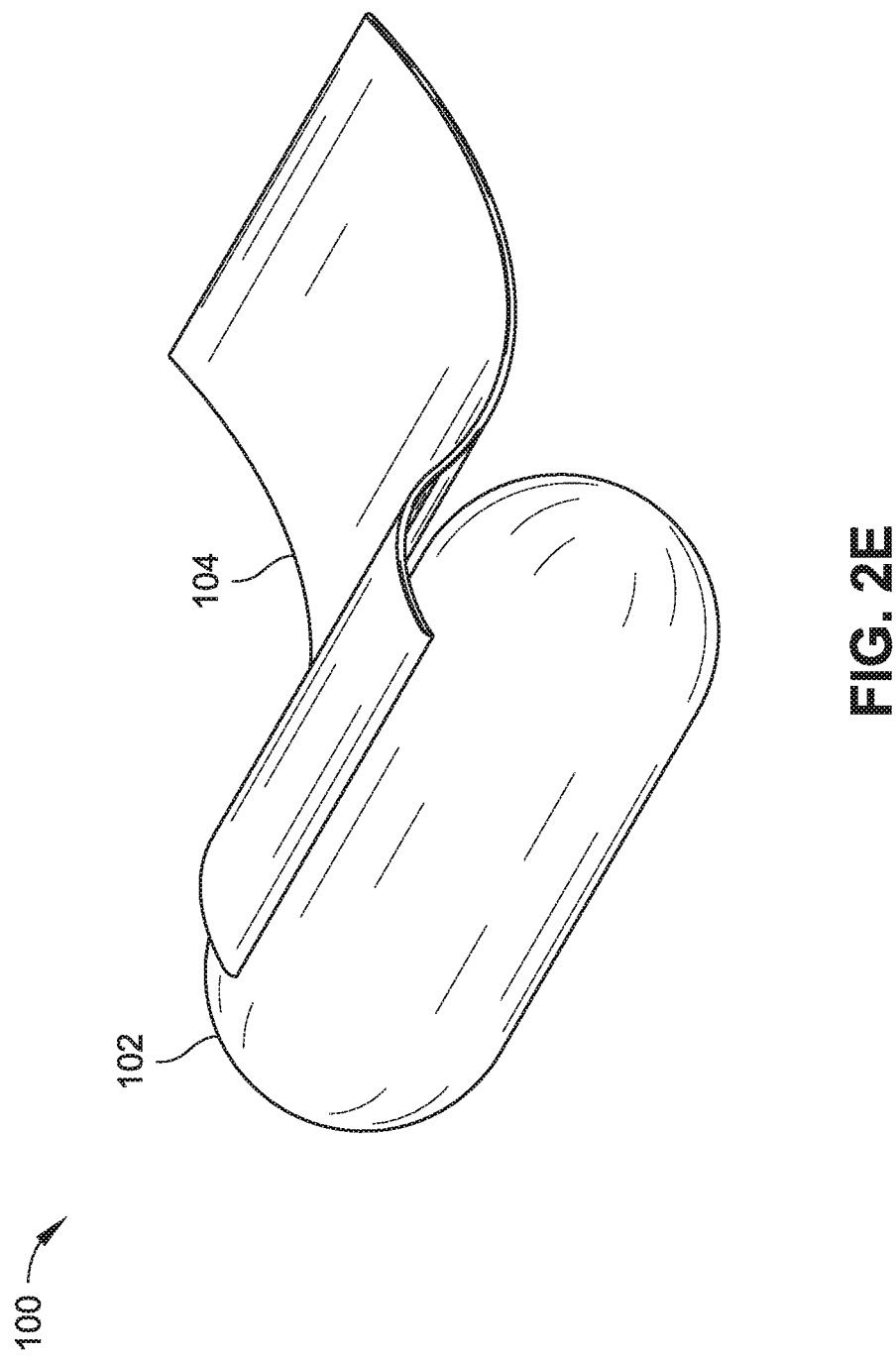
FIG. 2E is a schematic of an embodiment of an intraluminal device such as shown in FIG. 1.
Figure 2F:
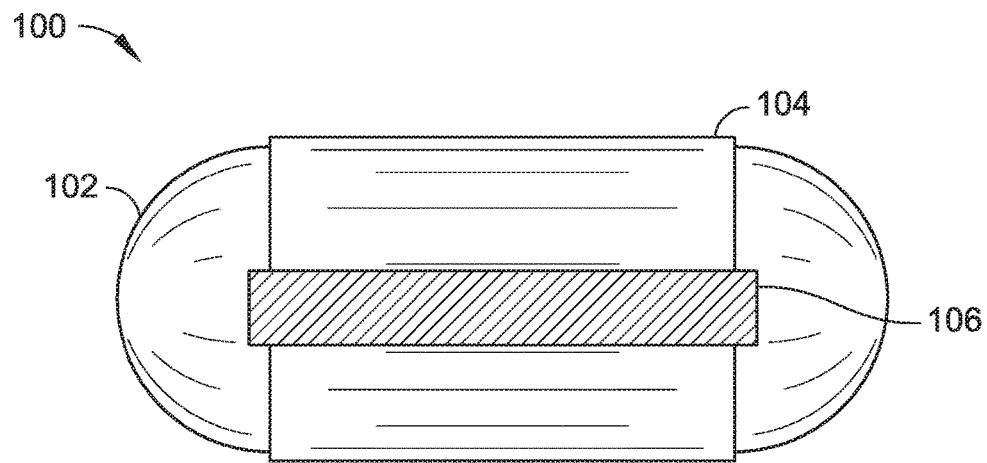
FIG. 2F is a schematic of an embodiment of an intraluminal device such as shown in FIG. 1.
Figure 3D:
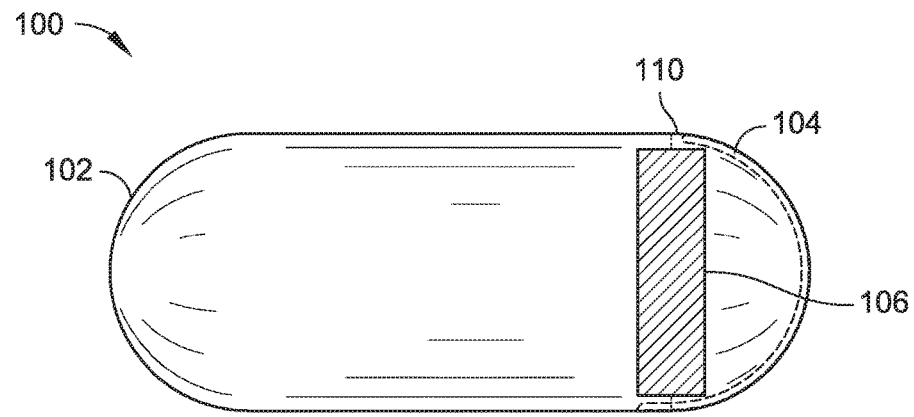
FIG. 3D is a schematic of an embodiment of an intraluminal device such as shown in FIG. 1.

In embodiments, the intraluminal device 100 includes a biodegradable or dissolvable barrier 106 (e.g., as shown in FIGS. 2F and 3D). For example, the barrier 106 can include a biodegradable or dissolvable adhesive patch, tape, or the like. The barrier 106 maintains the deployable element 104 in the first configuration until the barrier 106 is at least partially degraded or dissolved. The deployable element 104 or a removable portion 110 of the shell 102 can be released after the barrier 106 is at least partially degraded or dissolved, enabling the deployable element 104 to be actuated from the first configuration to a second (deployed) configuration.

Figure 2G:
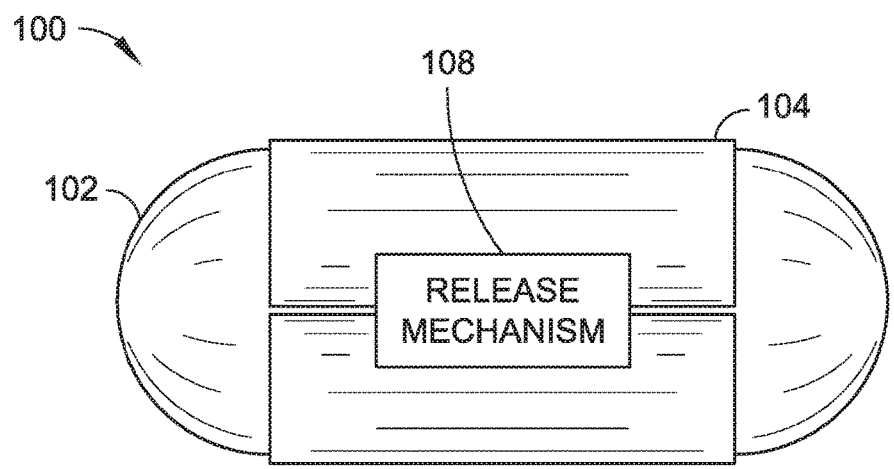
FIG. 2G is a schematic of an embodiment of an intraluminal device such as shown in FIG. 1.
Figure 3E:
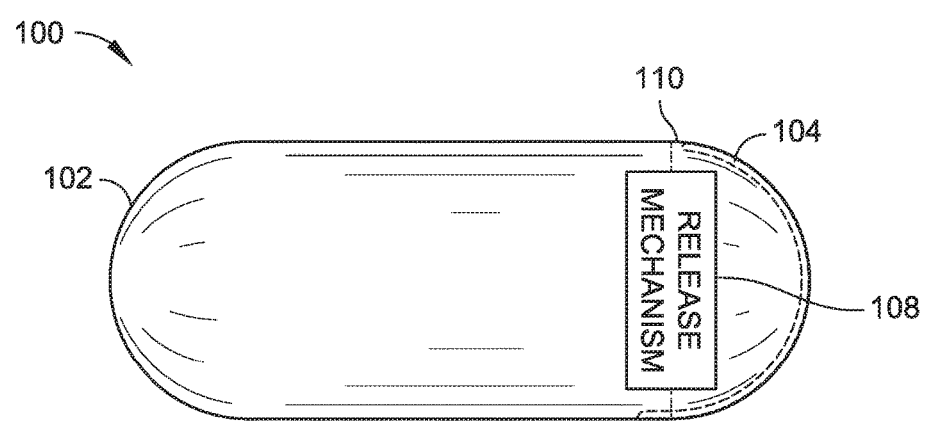
FIG. 3E is a schematic of an embodiment of an intraluminal device such as shown in FIG. 1.

In embodiments, the intraluminal device 100 includes a release mechanism 108 (e.g., as shown in FIGS. 2G and 3E). For example, the release mechanism 108 can include a latch, clasp, or other actuatable fastener that maintains the deployable element 104 in the first configuration until the release mechanism 108 is triggered. The release mechanism may be triggered by an actuator (e.g., actuator 242) driven by at least one of an electric current, an electric field, a magnetic field, fluid pressure, or mechanical spring force. For example, the release mechanism 108 can be triggered directly (or indirectly via the actuator 242) in response to an electric current, an electric field, a magnetic field, a chemical reaction, a temperature change, a pressure change, a physical process, or a biological process. When the release mechanism 108 is triggered, the deployable element 104 or a removable portion 110 of the shell 102 is released, enabling the deployable element 104 to be actuated from the first configuration to a second (deployed) configuration.

Figure 4:
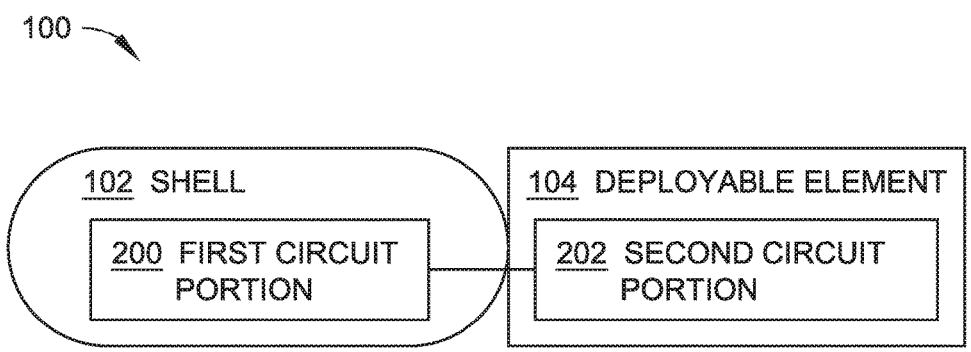
FIG. 4 is a schematic of an embodiment of an intraluminal device such as shown in FIG. 1.
Figure 13:
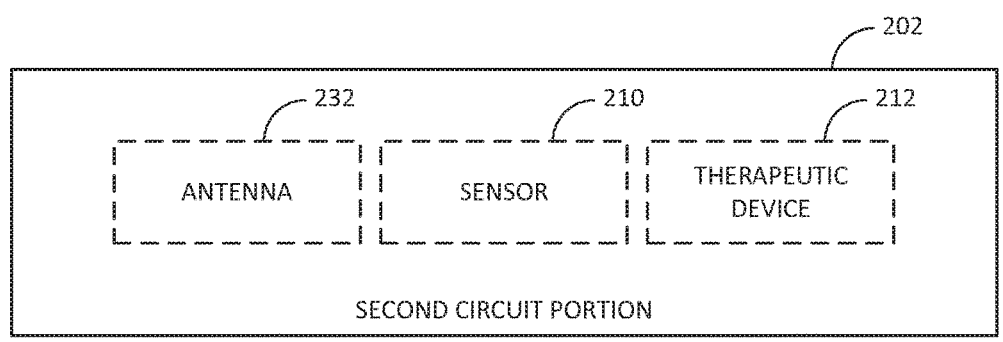
FIG. 13 is a schematic of an embodiment of circuitry or component structures implemented in or on a deployable element of an intraluminal device such as shown in FIG. 1.

Looking now to FIG. 4, the shell 102 can include a first circuit portion 200, and the deployable element 104 can include a second circuit portion 202. As used herein, a "circuit portion" is not limited to discrete circuit elements, assembled, or printed circuitry. The first circuit portion 200 and the second circuit portion 202 can also include sensors, therapeutic devices, energy storage devices, transmitters, receivers, transceivers, antennas, and so forth. The circuitry and any other components carried by the intraluminal device 100 are defined by the first circuit portion 200 and the second circuit portion 202 so as to be distributed between the shell 102 and the deployable element 104. In this regard, selected circuitry or components (i.e., the second circuit portion 202) are deployable from the shell 102. For example, as shown in FIG. 13, the second circuit portion 202 can include at least a portion of an antenna 232, a sensor 212, or a therapeutic device 210, or a combination thereof.

In embodiments, the second circuit portion 202 includes one or more of: a temperature sensor, a pH sensor, a flow rate sensor, an intraluminal pressure sensor, an analyte sensor, an imaging device (e.g., a camera or a scanner), an ultrasound transducer, an endoscopic surgical instrument, an endoscopic biopsy tool, an ablation tool, a radiation source, a syringe, a delivery tool, a fluid pump, a flow gradient sensor, a chemical gradient sensor, an electromagnetic radiation, sonic, or ultrasonic emitter or detector, or the like. In embodiments, an ablation tool may include a cutting tool, a laser, a heated tool, a dispenser of heated fluid, a cryotool, a dispenser of cooling fluid, an ultrasound transducer, a radio tool, or the like. Ablation can include removal of a tissue (e.g., a tumor or a lesion). Ablation can be performed, for example, by cutting, burning (e.g., thermal ablation as by a heating element or a laser), or freezing (e.g., cryoablation as by delivery of a cooling fluid) a tissue, or by delivering energy such as ultrasound energy or high frequency radio energy. For example, endovenous ablation using thermal or high frequency radio energy can be used to destroy tissue from within a blood vessel. In embodiments, a delivery tool may include any type of device able to deliver an agent such as a medicament. A delivery tool can include, for example, a passive delivery device (e.g., a reservoir, gel, or coating that releases an agent over time), an active delivery device (e.g., a programmed delivery device having a pump) or a responsive delivery device (e.g., a programmed delivery device in communication with a controller or a responsive gel delivery system).

The deployable element 104 can provide for enhanced dimensions (e.g., length, width, surface area, etc.) for components defined by the second circuit portion 202, among other possible advantages. Including the second circuit portion 202 in the deployable element 104 can provide advantages such as, but not limited to, greater surface area for an antenna coil or enhanced antenna length, greater sensor area or improved sensor contact with fluids in the biological lumen or with luminal walls, improved orientation of a therapeutic device, sensor, or antenna within the biological lumen, and so forth.

Figure 5A:
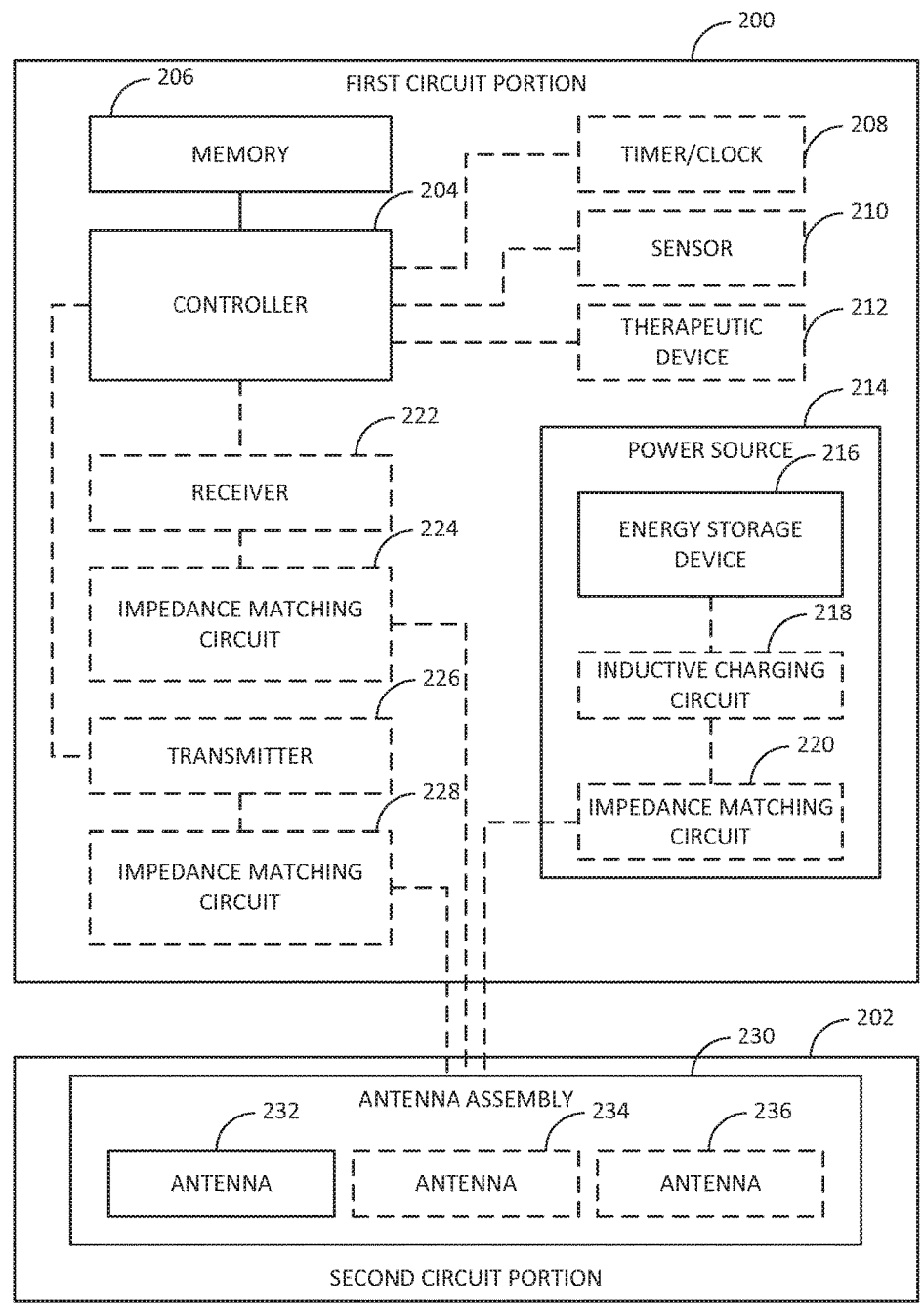
FIG. 5A is a schematic of an embodiment of an intraluminal device such as shown in FIG. 1.
Figure 5B:
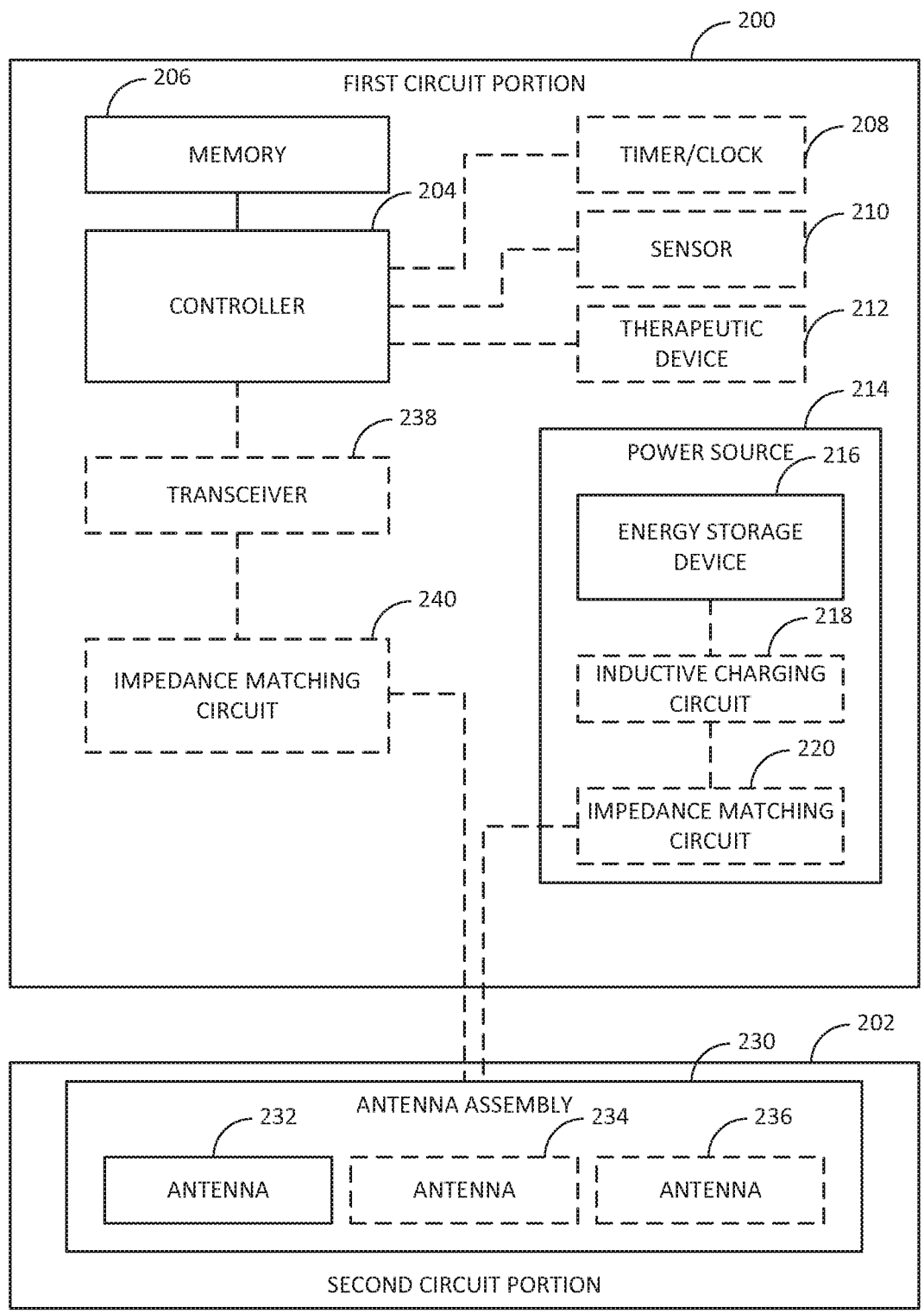
FIG. 5B is a schematic of an embodiment of an intraluminal device such as shown in FIG. 1.

Embodiments of the first circuit portion 200 and the second circuit portion 202 are shown in FIGS. 5A and 5B. The first circuit portion 200 includes a controller 204 having a memory 206. The memory 206 can include program instructions (e.g., software modules executable by the controller 204) with sets of instructions for performing the controller operations described herein. The controller 204 can include at least one microprocessor, central processing unit (CPU), microcontroller, digital signal processor (DSP), application-specific integrated circuit (ASIC), field programmable gate entry (FPGA), or the like, or any combinations thereof, and can include discrete digital or analog circuit elements or electronics, or combinations thereof. In embodiments, controller 204 includes one or more ASICs having a plurality of predefined logic components. In embodiments, the controller 204 includes one or more FPGAs having a plurality of programmable logic commands.

Figure 6:
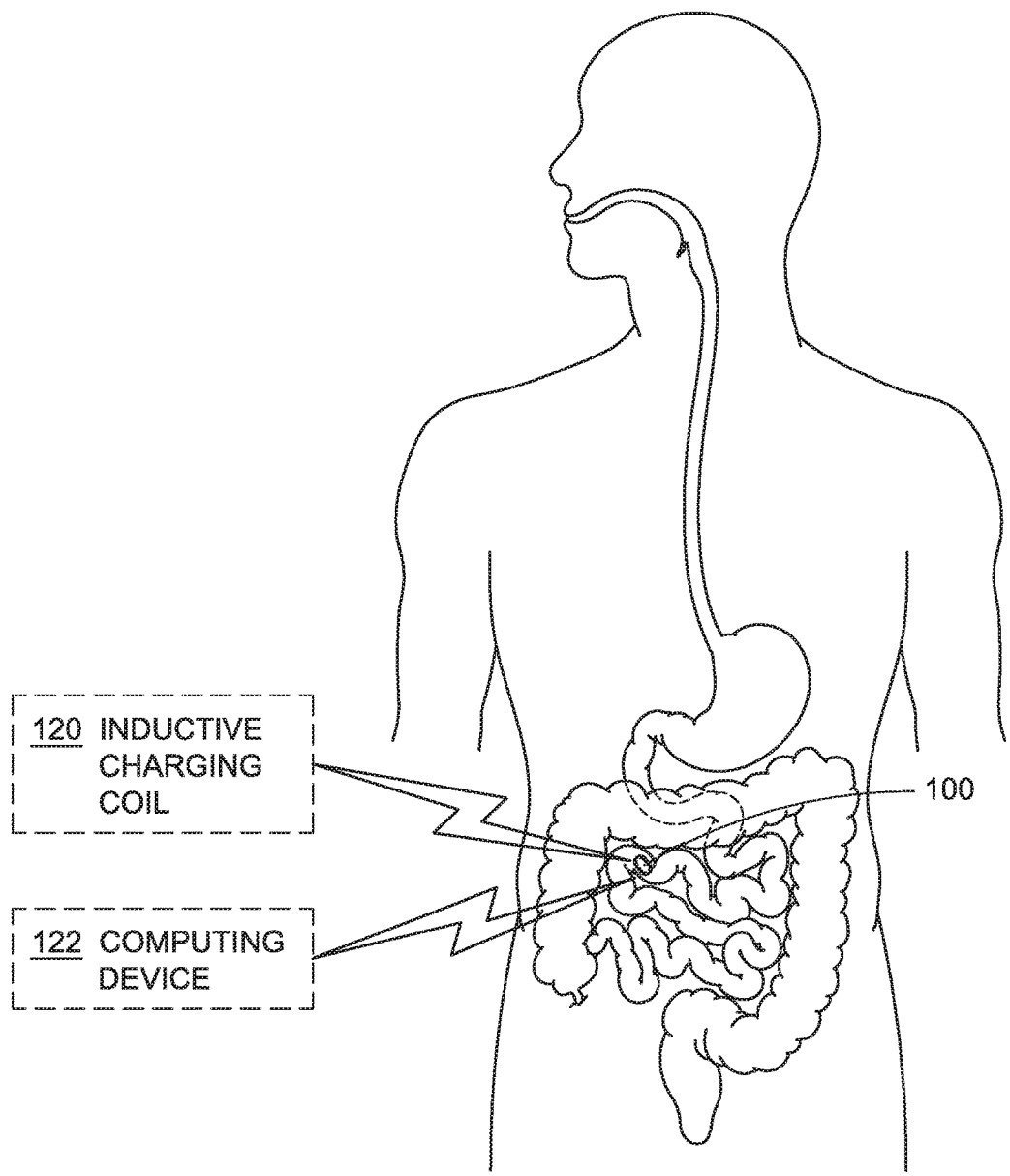
FIG. 6 is a system for sending or receiving electromagnetic signals to or from an intraluminal device such as shown in FIG. 1.

In embodiments, the controller 204 is operably coupled to the sensor 210 (which can be at least partially disposed in the first circuit portion 200 or the second circuit portion 202, or both) and is configured to receive the one or more sense signals from the sensor 210. In embodiments, the controller 204 can store information regarding the one or more sense signals in the memory 206. In embodiments, the controller can send the send information regarding the one or more sense signals to an external device (e.g., an external computing device 122, as shown in FIG. 6).

The sensor 210 can be oriented in the shell 102 or the deployable element 104 to detect at least one characteristic of the biological lumen and to generate one or more sense signals. In embodiments, the sensor 210 generates the one or more sense signals upon detection of at least one characteristic of the biological lumen. In embodiments, the sensor 210 constantly generates sense signals, even when no characteristics of the biological lumen are observed (e.g., null signals). In embodiments, the controller 204 is configured to receive the one or more sense signals based upon a predetermined schedule (e.g., based upon an input from a timer/clock 208 within or connected to the controller 204), a biological map (e.g., when the intraluminal device 100 is in at a position of interest), information or commands received from the external computing system 122, or the like. The sensor 210 can include, but is not limited to, at least one of an optical device (e.g., an optical sensor such as a near infrared sensor or laser, or an imaging device such as a camera), a physiological sensor (e.g., a pH sensor, temperature sensor, oximeter, pressure sensor, electrical conductivity sensor, etc.), a pH sensor (e.g., to detect a pH indicating position within a gastrointestinal tract), a pressure sensor, a temperature sensor (e.g., to detect whether the device is in the body or has been eliminated), a chemical sensor, a biosensor, a flow rate sensor, an analyte sensor, a flow gradient sensor, a chemical gradient sensor, an ultrasound transducer, or an electromagnetic radiation, sonic, or ultrasonic emitter or detector. A physiological sensor can include a sensor able to measure a physiological parameter; for example, physiological parameters in the gastrointestinal tract that are routinely of interest to physicians include temperature, pH, pressure, oxygenation, and electrical conductivity, while a physiological parameter of the viscosity of mucus (e.g., identified by imaging) would be of interest in a respiratory tract of a cystic fibrosis patient.

Physiological sensors can include chemical sensors and biosensors. For example, without limitation, a chemical sensor can detect a chemical signature of an analyte, for example an analyte of a physiological origin (e.g., a cellular mm compound, a secreted compound such as an antibody or a cytokine, or a metabolite) or an analyte of an exogenous origin (e.g., an ingested or inhaled substance, such as a drug, or a tagging or labeling compound such as might be released from the intraluminal device 100 or provided separately). Examples of chemical sensors include, but are not limited to, sensors having recognition elements, electronic chip sensors, microbalance sensors, and near infrared spectrometers. A biosensor can detect a biochemical or biological element. Biosensors include, for example but are not limited to, sensors having a biological recognition element able to bind an analyte of interest (e.g., an aptamer-based microcantilever) and sensors utilizing an enzyme with recognition and reaction properties. In embodiments, chemical sensors or biosensors can include molecular sensor or nanosensor aspects.

In embodiments, sensors 210 can include an emitter and a detector operable to emit and detect at least one of electromagnetic signals (e.g., visible light, infrared, or other illumination signals, radio frequency (RF) signals, microwave energy signals, etc.), audible signals, ultrasonic signals, or the like. In embodiments, the deployable element includes an emitter, and the shell includes a detector, or vice versa. This can allow for collecting reflected, refracted, or scattered signals (e.g., for time of flight measurements) at an expanded range of angles or can allow for collecting the reflected, refracted, or scattered signals while the intraluminal device 100 is traveling through the biological lumen (e.g., where the signal is emitted from the shell 102 at a first position and collected at the deployable element 104 while the shell 102 is at a second position).

In embodiments, the controller 204 is operably coupled to the therapeutic device 212 (which can be at least partially disposed in the first circuit portion 200 or the second circuit portion 202, or both) and is configured to provide one or more control signals for the therapeutic device 212. In embodiments, the controller 204 is configured to control the therapeutic device 212 in accordance with one or more control modules stored in the memory 206. For example, a control module can include program instructions for actuating the therapeutic device 212 based on a predetermined schedule (e.g., based upon an input from the timer/clock 208), a biological map (e.g., when the intraluminal device 100 is in at a position of interest), information from sensor 210 (e.g., based upon a detecting a temperature, a pH, a flow rate, an intraluminal pressure, presence of an analyte, an intraluminal image, an ultrasound reading, etc.), information or commands received from the external computing system 122, or the like. In embodiments, the therapeutic device 212 includes, but is not limited to, one or more of: an ultrasound transducer, an endoscopic surgical instrument (e.g., endoscopic cutting tool, stapler, suturing tool, grasper, etc.), an endoscopic biopsy tool (e.g., biopsy needle), an ablation tool, a radiation source (e.g., laser), a syringe, a delivery tool, or a fluid pump (e.g., insulin pump or the like).

In embodiments, the controller 204 is coupled to a data receiver 222 that is at least partially included in at least one of the first circuit portion 200 or the second circuit portion 202. For example, the data receiver 222 can be included in the first circuit portion 200 and connected with an antenna (e.g., antenna 232, 234, or 236) that is at least partially included in the second circuit portion 202. In embodiments, the second circuit portion 202 includes an antenna assembly 230 with one or more antennas (e.g., antennas 232, 234, and 236) to provide a deployable antenna assembly, the antenna assembly 230 provides one or more antennas with, for example, improved length, surface area, or orientation when the antenna assembly 230 is deployed (i.e., when the deployable element 104 is actuated from the first configuration to the second configuration). The receiver 222 can receive one or more data signals associated with requests for information or control commands/instructions from the externally located computing device 122. For example, the receiver 222 can receive queries for information from the sensor 210, commands/instructions for actuating or otherwise controlling the therapeutic device 212, commands/instructions for actuating the deployable element 104 (e.g., commands/instructions for driving an actuator 242 that triggers the release mechanism 108, or for driving the actuator 242 to extend, unfold, unwrap, or otherwise actuate the deployable element 104 from the first configuration to at least the second configuration), or commands/instructions for navigating the intraluminal device 100 (e.g., commands/instructions for actuating a motive structure that allows controlled motility of the intraluminal device 100 through the lumen of the biological subject).

An impedance-matching circuit 224 can be connected between the receiver 222 and a respective antenna (e.g., antenna 232, 234, or 236). The impedance-matching circuit 224 can reduce signal reflections between the receiver 222 and the respective antenna by matching the input impedance of the receiver 222 to the output impedance of the respective antenna. In embodiments, the impedance-matching circuit 224 can include an adaptive impedance-matching circuit with at least one of an automatically adjustable capacitance, an automatically adjustable inductance, or an automatically adjustable impedance. The impedance-matching circuit 224 can adaptively match the impedance to account for changes caused by parasitic capacitance, antenna orientation, position in the biological lumen, or other factors that can directly or indirectly affect signal performance.

In embodiments, the controller 204 is coupled to a data transmitter 226 that is at least partially included in at least one of the first circuit portion 200 or the second circuit portion 202. For example, the data transmitter 226 can be included in the first circuit portion 200 and connected with an antenna (e.g., antenna 232, 234, or 236) that is at least partially included in the second circuit portion 202. The data transmitter 226 can wirelessly transmit one or more data signals associated with the one or more sense signals from the sensor 210 responsive to instruction by the controller 204. For example, the data transmitter 226 can transmit the one or more data signals based on a predetermined schedule (e.g., based upon an input from the timer/clock 208), a biological map (e.g., when the intraluminal device 100 is in at a position of interest), information from sensor 210 (e.g., based upon a detecting a temperature, a pH, a flow rate, an intraluminal pressure, presence of an analyte, an intraluminal image, an ultrasound reading, etc.), a request for information or query received from the external computing system 122, or the like.

An impedance-matching circuit 228 can be connected between the data transmitter 226 and a respective antenna (e.g., antenna 232, 234, or 236). The impedance-matching circuit 228 can reduce signal reflections between the data transmitter 226 and the respective antenna by matching the output impedance of the data transmitter 226 to the input impedance of the respective antenna. In embodiments, the impedance-matching circuit 228 can include an adaptive impedance-matching circuit with at least one of an automatically adjustable capacitance, an automatically adjustable inductance, or an automatically adjustable impedance. The impedance-matching circuit 228 can adaptively match the impedance to account for changes caused by parasitic capacitance, antenna orientation, position in the biological lumen, or other factors that can directly or indirectly affect signal performance.

As shown in FIG. 5B, the receiver 222 and the transmitter 226 circuitry and components can be at least partially combined, where the intraluminal device includes a transceiver 238 coupled to the controller 204. The transceiver 238 can be configured as the receiver 222 and the transmitter 226 are configured in embodiments described herein. For example, the transceiver 238 can be included in the first circuit portion 200 and connected with one or more antennas (e.g., at least one of antenna 232, 234, or 236) that is at least partially included in the second circuit portion 202. The transceiver 238 can also be coupled with at least one impedance-matching circuit 240. The impedance-matching circuit 240 can reduce signal reflections between the transceiver 238 and the respective antenna or antenna set by matching the output/input impedance of the transceiver 238 to the input/output impedance of the respective antenna or antenna set. In embodiments, the impedance-matching circuit 240 can include an adaptive impedance-matching circuit with at least one of an automatically adjustable capacitance, an automatically adjustable inductance, or an automatically adjustable impedance. The impedance-matching circuit 240 can adaptively match the impedance to account for changes caused by parasitic capacitance, antenna orientation, position in the biological lumen, or other factors that can directly or indirectly affect signal performance.

The intraluminal device 100 includes a local power source 214 for furnishing electrical power to one or more components of the intraluminal device 100. The local power source 214 can furnish electrical power for one or more of: the controller 204, memory 206, timer/clock 208, sensor 210, therapeutic device 212, receiver 222, transmitter 226, transceiver 238, actuator 242, impedance-matching circuitry, and any other circuitry, component, or device that utilizes electrical power and is carried by the shell 102 or the deployable element 104. In embodiments, the local power source 214 includes a local generator (e.g., a mechanical, chemical, or thermal energy harvesting system). In embodiments, the local power source 214 includes an energy storage device 216, such as a battery, a microbattery, an electrochemical battery, a fuel cell, a capacitive energy storage device (e.g., capacitor), an electromagnetic storage device (e.g., inductor), or the like.

In embodiments, the local power source 214 includes an inductive charging circuit 218 coupled to the energy storage device 216 and configured to wirelessly receive energy from an inductive charging coil 120 (e.g., such as an RF inductive charger, Wireless Power Consortium (WPC), or Qi inductive charger, microwave transmitter, or the like). For example, the inductive charging circuit 218 receives wireless energy signals from the inductive charging coil 120 or other wireless energy source via a respective antenna or coil (e.g., antenna 232, 234, or 236) and furnishes at least a portion of the collected energy to charge the energy storage device 216. In embodiments, the inductive charging circuit 218 can also be configured to directly power one or more components of the intraluminal device 100 by furnishing at least a portion of the collected energy. In embodiments, the inductive charging circuit 218 and at least one of the data receiver 222 or the data transmitter 226 (or data transceiver 238) may include shared structural components, for example, to facilitate reception of power signals and reception/transmission of data signals with a shared antenna, shared impedance-matching circuitry, or a combination thereof.

The inductive charging coil 120 may be external to the biological lumen of the subject (e.g., as shown in FIG. 6). For example, the inductive charging coil 120 can be located external to the body of the biological subject or at least partially implanted in the biological subject (e.g., adjacent to the biological lumen containing the intraluminal device 100). In embodiments, the charging coil 120 can be inside the biological lumen. For example, the charging coil 120 can be anchored to a luminal wall or carried by a second intraluminal device (e.g., as described in U.S. patent application Ser. Nos. 15/051,088 and 15/051,126, which are incorporated herein by reference in their entireties).

An ability to increase dimensions of the antenna or coil coupled to the inductive charging circuit 218 can provide for improved inductive coupling with the inductive charging coil 120. Thus, the deployable element 102 can actuate from the first configuration to the second configuration to deploy the antenna assembly 230 when the inductive charging circuit 218 is in an active state. In embodiments, the controller 204 can trigger deployment of the antenna assembly 230 to facilitate inductive charging for the intraluminal device 100. For example, the controller 204 can cause the antenna assembly 230 to deploy when the computing device 122 provides an indication that the inductive charging coil 120 is active, or in response to a programmed schedule, timer setting, sensor reading (e.g., indicating a location of the intraluminal device 100), or a sensed, detected, or reported energy storage level (e.g., low battery level) of the energy storage device 216.

In embodiments, an impedance-matching circuit 220 is connected between the inductive charging circuit 218 and a respective antenna (e.g., antenna 232, 234, or 236). The impedance-matching circuit 220 can reduce signal reflections between the inductive charging circuit 218 and the respective antenna by matching the input impedance of the inductive charging circuit 220 to the output impedance of the respective antenna. The impedance-matching circuit 220 can also include tuner circuitry that enables the antenna to be tuned to a frequency (e.g., resonant frequency) of the inductive charging coil 120. In embodiments, the impedance-matching circuit 220 can include an adaptive impedance-matching circuit with at least one of an automatically adjustable capacitance, an automatically adjustable inductance, or an automatically adjustable impedance. The impedance-matching circuit 220 can adaptively match the impedance to account for changes caused by parasitic capacitance, antenna orientation, position in the biological lumen, or other factors that can directly or indirectly affect signal performance.

FIG. 6 shows the computing device 122 communicating with the intraluminal device 100. For example, the computing device 122 can be positioned external to the body of the individual subject to provide control signals to one or more components of the intraluminal device 100. In embodiments, the computing device 122 is operable to send one or more control signals to the data receiver 222 (or transceiver 238) of the intraluminal device 100. The controller 204 can receive the control signals from the computing device 122 for execution of the commands, including, but not limited to, collecting/transmitting information from the sensor 210, activating/deactivating the therapeutic device 212, activating/deactivating the inductive charging circuit 218 to transfer of energy or cease of transfer of energy from the inductive charging coil 120, actuating the deployable element 104 from the first configuration to at least the second (deployed) configuration, repositioning of intraluminal device 100, or the like. In embodiments, the computing device 122 includes a communication device, such as one or more of a mobile communication device or a computer system including, but not limited to, mobile computing devices (e.g., hand-held portable computers, Personal Digital Assistants (PDAs), laptop computers, netbook computers, tablet computers, or so forth), mobile telephone devices (e.g., cellular telephones and smartphones), devices that include functionalities associated with smartphones and tablet computers (e.g., phablets), portable game devices, portable media players, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, and other devices that employ touch-based human interfaces. The computing device 122 can communicate (e.g., send and receive communication signals) with the intraluminal device 100 via one or more connected or wireless communication mechanisms including, but not limited to acoustic communication signals, optical communication signals, radio communication signals, infrared communication signals, ultrasonic communication signals, or the like. For example, the computing device 122 may include an antenna coupled with a transmitter, receiver, or transceiver for sending or receiving wireless communications.

Figure 7:
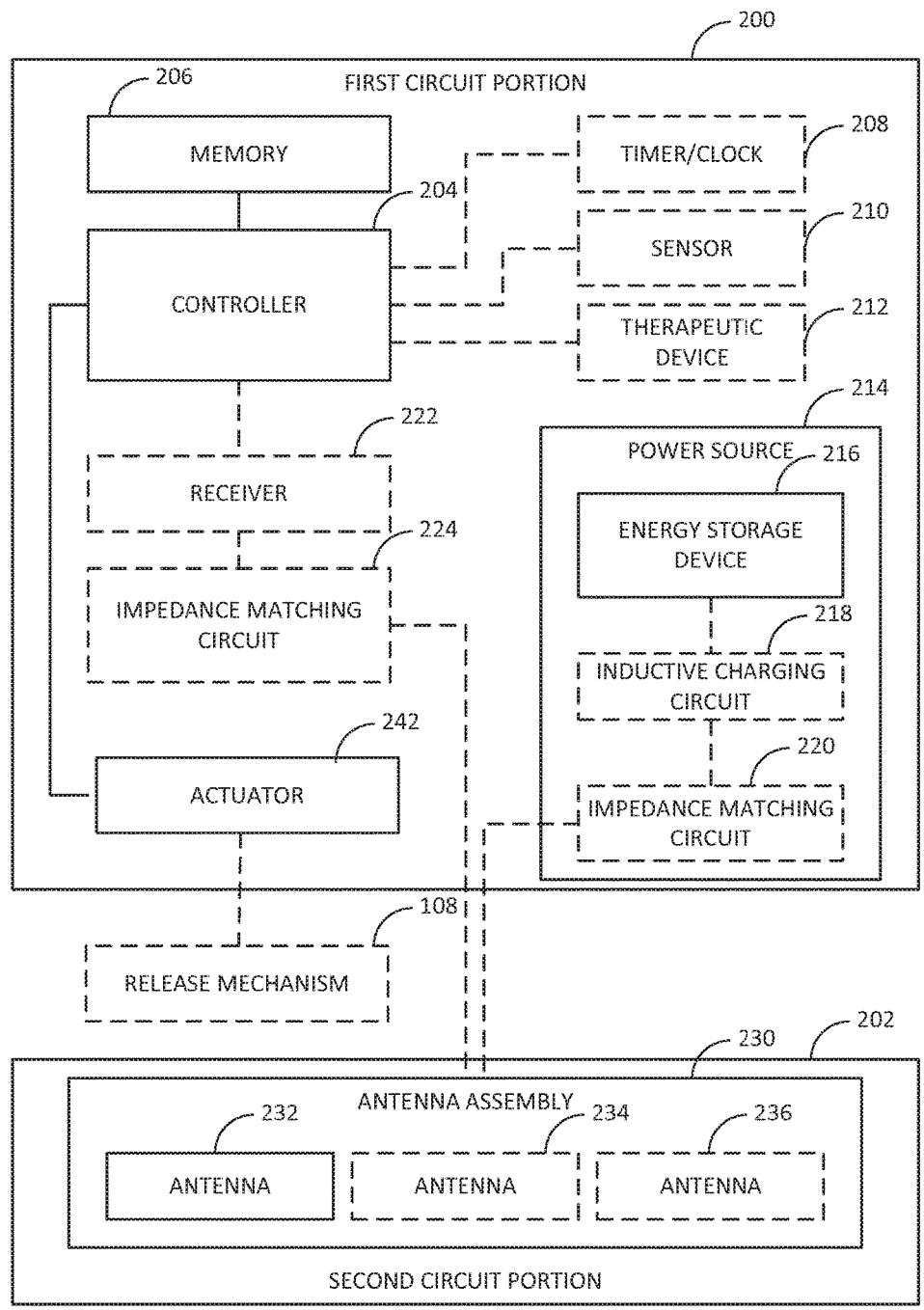
FIG. 7 is a schematic of an embodiment of an intraluminal device such as shown in FIG. 1.

As shown in FIG. 7, the actuator 242 can be configured to trigger the release mechanism 108 to deploy the deployable element 104. For example, the actuator 242 can trigger the release mechanism 108 by causing the release mechanism to unlatch or unfasten in response to a mechanical or electromagnetic force applied by the actuator 242, thereby releasing the deployable element 104. In embodiments, the actuator 242 can directly actuate the deployable element 104 from the first configuration to the second configuration. For example, the actuator 242 can apply force to one or more portions of the deployable element 104. The actuator 242 can apply at least one of an electric current, an electric field, a magnetic field, fluid pressure, or mechanical spring force to actuate the deployable element 104 from the first configuration to the second configuration. For example, the actuator 242 can include, but is not limited to, a mechanical actuator, a fluid-driven actuator, a chemical actuator, an electromechanical actuator, a magnetic actuator, or an electromagnetic actuator. In embodiments the actuator 242 is driven in response to at least one of an electric current, an electric field, a magnetic field, a chemical reaction, a temperature change, a pressure change, a physical process, or a biological process. For example, the actuator 242 can be driven by controller 204 in response to an input from sensor 210. In embodiments, the actuator 242 can be driven by controller 204 in response to an input from timer/clock 208 or in response to a communication received from the computing device 122.

In embodiments, the actuator 242 includes at least one smart material or responsive material. For example, the actuator 242 can include an electroactive polymer, a magnetoactive polymer, an ionic composite polymer, an electrorheological fluid, magnetorheological fluid, or a shape memory alloy. For example, an electroactive polymer actuator can include one or more dielectric electroactive polymer such as one or more ferroelectric polymers (e.g., copolymers comprising polyvinylidene difluoride ("PVDF")), dielectric elastomers, electrostrictive graft elastomers, or liquid crystalline polymers. For example, an electroactive polymer actuator can include one or more ionic electroactive polymer such as one or more conductive polymers, ionic polymer-metal composites (IPMCs), or responsive gels. For example, an electroactive actuator can include carbon structures (including nanostructures). For example, a magnetoactive polymer actuator can include a polymer with embedded magnetic or paramagnetic particles. For example, an actuator of a shape memory material can include a nickel-titanium shape memory alloy, such as nitinol or other suitable nickel-titanium alloy composition. In embodiments, the actuator 242 including at least one smart material or responsive material is responsive to an electric current, an electric field, or a magnetic field. In embodiments, the actuator 242 includes one or more micro-electro-mechanical actuators. For example, the one or more micro-electro-mechanical actuators can include one or more micro-piezoelectric actuators, one or more micro-electrostatic actuators, or one or more micro-electromagnetic actuators. As another example, one suitable micro-piezoelectric actuator is New Scale's SQUIGGLE™ motor.

In embodiments, the intraluminal device 100 includes a motive structure operable to provide movement (e.g., alteration of position, orientation, etc.) to the intraluminal device 100. As described herein, the positioning and/or orientation of the intraluminal device 100 can influence power transfer conditions, sense conditions, communication conditions, and so forth. The motive structure can include, but is not limited to, one or more of an oscillatory motive mechanism, a vibratory motive mechanism, an actuator-driven bending mechanism, a unimorph actuator, a bimorph actuator, a pneumatic bellow, a lumen-surface-engaging structure, an impelling device, or a jointed appendage. For example, in embodiments, the intraluminal device 100 includes at least one inchworm-like motive mechanism, in which at least a portion of the intraluminal device 100 intermittently engages and disengages from the surface thereby traversing a distance. For example, the intraluminal device 100 can include an inchworm motor. For example, the intraluminal device 100 can include an inchworm actuator. For example, the intraluminal device 100 can include a stick and slip mechanism. In embodiments, the intraluminal device 100 includes at least one earthworm-like motive mechanism, in which at least a portion of the intraluminal device 100 is adjacently displaced along the surface thereby traversing a distance. In embodiments the intraluminal device 100 includes mechanism inducing forced bending vibrations of continua of the intraluminal device 100 driven by actuators such as piezoelectric bending actuators. The locomotion direction of the intraluminal device 100 can be controlled by the excitation frequencies of the actuation element. In embodiments, the intraluminal device 100 may include a piezoelectric unimorph actuator or a piezoelectric bimorph actuator. In embodiments, the intraluminal device 100 can include at least one actuator that drives the movement of at least a portion of the intraluminal device 100 and the engagement of the surface. For example, the intraluminal device 100 might include two-way linear actuators using springs made from a shape memory alloy. For example, the intraluminal device 100 might include a piezoelectric microactuator. For example, the intraluminal device 100 might include a micromotor. In embodiments the intraluminal device 100 is jointed between sections of the intraluminal device 100, and one or more actuators drive each section, for example in an inchworm- or earthworm-like fashion. In embodiments, the intraluminal device 100 includes an expandable bellow, for example, a pneumatic bellows, that provides the locomotive mechanism. In embodiments, the intraluminal device 100 includes surface-engaging protrusions, microprotrusions, setae, micropilli, or adhesive micropilli. In embodiments, at least a portion of the intraluminal device 100 includes micro-patterning on the surface, e.g., for friction enhancement. In embodiments, the intraluminal device 100 includes at least one motive mechanism configured to touch, grasp, grip, or otherwise engage the surface tissue of the lumen.

In embodiments, the impelling device is configured to engage the lumen tissue and provide locomotion to the intraluminal device 100; for example, an impelling device might comprise one or more appendages, legs, or wheels, with or without adhesive aspects, e.g., adhesive micropilli. One or more actuators or motors can be used to drive impelling devices. Examples of actuators include piezoelectric, DC motors, electromagnetic, and electrostatic actuators. In addition, actuators can be formed from shape memory alloys or ionic polymer metal components. In embodiments, the intraluminal device 100 includes jointed appendages and legs that can be actuated to propel the intraluminal device 100 forward in a walking or crawling motion. For example, a legged locomotion system can include a slot-follower mechanism driven via lead screw to provide propulsive force to a jointed leg. For example, multiple jointed legs, e.g., of superelastic or other material, can be motivated to interact with the surface under control of a motor, e.g., a brushless mini-motor. For example, appendages or legs can be formed from shape memory alloy and driven by the application of current. For example, appendages can act to engage the surface driven by rotational forces to provide locomotion. For example, wheels can be driven by motors or other actuators. In embodiments, actuators include microelectromechanical systems.

In embodiments, the intraluminal device 100 includes a steering mechanism. For example, the steering mechanism can be operable to alter a direction of travel of the intraluminal device 100. The steering mechanism can be utilized as an alternative to the motive structure or in addition to the motive structure (e.g., to provide directional change during motion). For example, in embodiments, the intraluminal device 100 is configured to employ one or more impelling mechanisms in a manner to provide movement in a particular direction. For example, to change direction (e.g., as directed by a controller), only a portion of multiple appendages (or legs or wheels) can be actuated, thereby moving a portion of the intraluminal device 100 so that the intraluminal device 100 heads in a new direction and allowing the intraluminal device 100 to be steered. In embodiments the intraluminal device 100 includes one or more arrays of impelling mechanisms. For example, the intraluminal device 100 may include an array of impelling mechanisms aligned along an x-axis and a second array of impelling mechanisms aligned along a y-axis.

In embodiments, the intraluminal device 100 includes a motion-resistive mechanism. For example, the motion-resistive mechanism is operable to resist a motion of the intraluminal device, such as to slow or stop the intraluminal device within the biological lumen. In embodiments, the motion-resistive mechanism includes a wall-engaging structure configured to engage a wall of the biological lumen to secure the intraluminal device 100 with respect to the wall of the biological lumen. For example, the wall-engaging structure includes at a structural component configured to physically interact with (e.g., grasp, adhere to, etc.) the wall of the biological lumen to resist motion of the intraluminal device 100, such as to anchor the intraluminal device 100, at least temporarily, with respect to the wall of the biological lumen.

Figure 8:
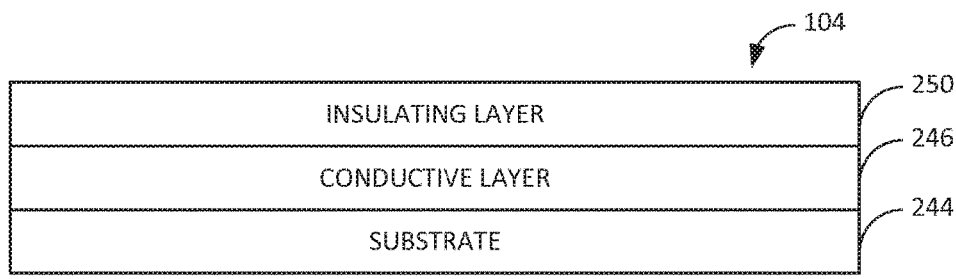
FIG. 8 is a schematic of an embodiment of a deployable element of an intraluminal device such as shown in FIG. 1.
Figure 16:
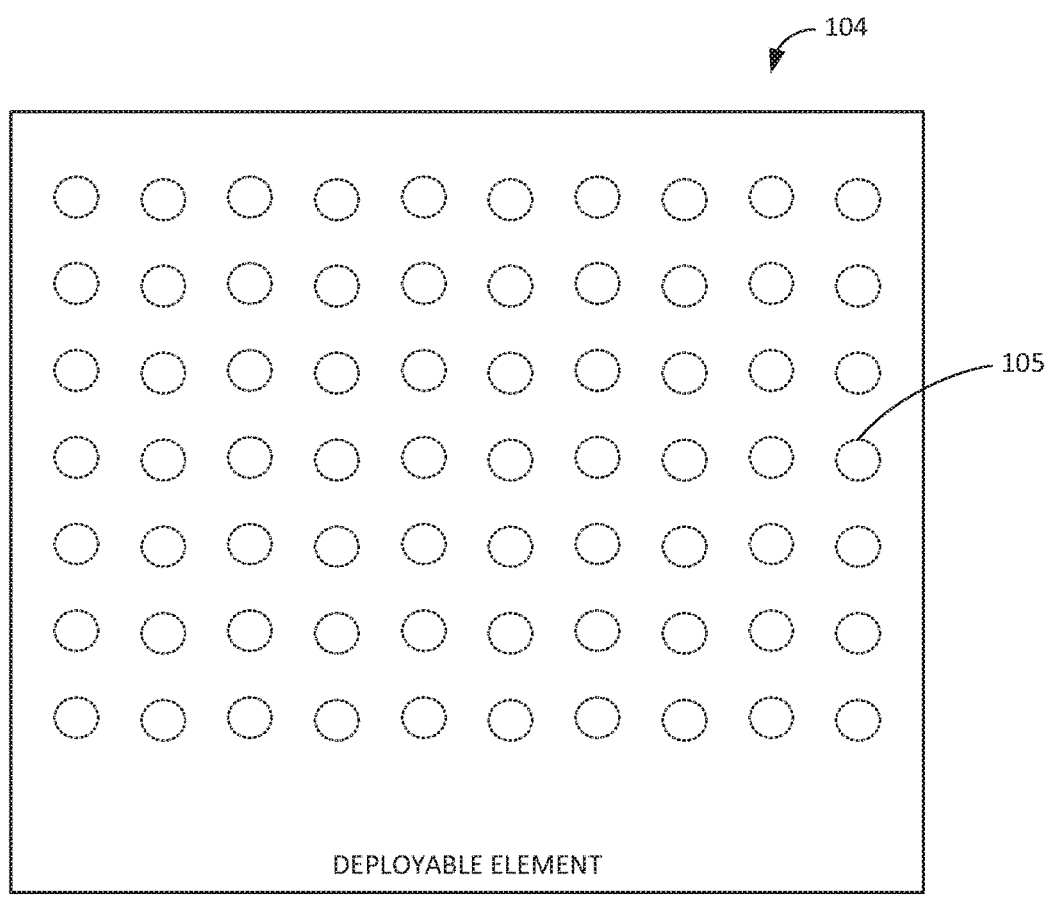
FIG. 16 is a schematic of an embodiment of a deployable element of an intraluminal device such as shown in FIG. 1.

FIG. 8 shows an embodiment of the deployable element 104. In embodiments, the deployable element 104 includes a flexible substrate 244 (e.g., a biocompatible or biodegradable substrate) with a conductive layer 246 disposed upon the flexible substrate 244. The conductive layer 246 defines a conductive trace or distribution of conductive elements. For example, the conductive layer 246 can include a conductive trace that is printed or formed by etching of the conductive layer 246 on the flexible substrate 244. The conductive layer 246 can also include a material that is at least one of non-toxic, biocompatible, or biodegradable. For example, the conductive layer 246 can include gold or another non-toxic metal or alloy. The deployable element 104 can further include an insulating layer 250 that insulates the conductive layer 246 from fluid or other substances in the biological lumen. The insulating layer 250 can include a second substrate or an epoxy that encapsulates the conductive layer 246 in between the insulating layer 250 and the flexible substrate 244. In embodiments, such as the embodiment shown in FIG. 16, the deployable element 104 (e.g., the flexible substrate 244 and other layers formed thereon) includes pores, slits, or other openings 105 to allow intraluminal fluid to flow therethrough. The openings 105 can be formed through portions of the deployable element 104 that are free of conductive material (e.g., portions that do not interfere with any conductive trace).

Figure 9A:
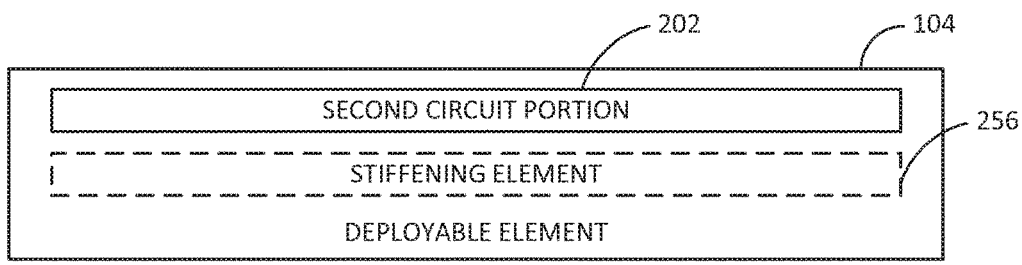
FIG. 9A is a schematic of an embodiment of a deployable element of an intraluminal device such as shown in FIG. 1.
Figure 9B:
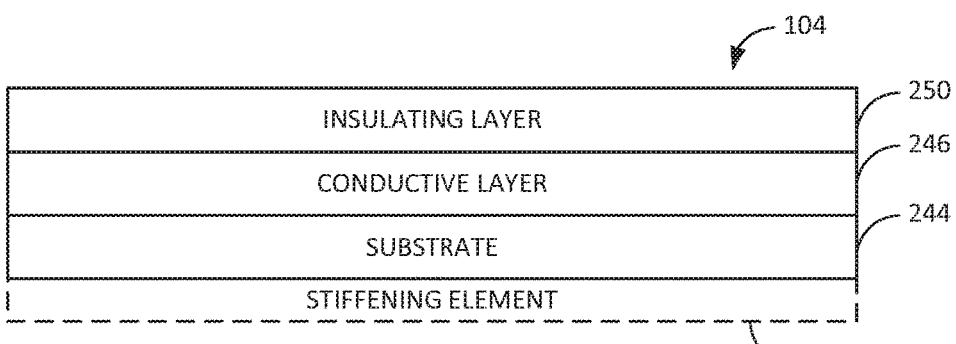
FIG. 9B is a schematic of an embodiment of a deployable element of an intraluminal device such as shown in FIG. 1.

As shown in FIGS. 9A and 9B, the deployable element 104 can include a stiffening element 256 that supports the deployable element 104 in the second (e.g., extended, unwrapped, or unfolded) configuration after the deployable element 104 is actuated or released from the first configuration, or otherwise deployed. For example, the stiffening element 256 includes at least one of a spring-like support structure (e.g., a resilient element), an inflatable support structure (e.g. a balloon-like element), or a fluid-carrying support structure (e.g. a sponge-like or balloon-like element). In embodiments, the stiffening element includes 256 a fluid-carrying support structure that is configured to be selectively filled with intraluminal fluid by a micro-pump or by osmotic or capillary fluid movement. The stiffening element 256 may be adjacent to the flexible substrate 244 (e.g., as shown in FIG. 9B) or adjacent to the insulating layer 250. In embodiments, the stiffening element 256 can comprise at least a portion of the flexible substrate 244 or the insulating layer 250. In embodiments, the stiffening element 104 includes supportive structure that is formed along a length of the deployable element 104, where the deployable element 104 does not include a flexible substrate, for example, where the deployable element 104 is tubular, string or thread like, or otherwise structured.

In embodiments, the stiffening element 256 includes at least one smart material or responsive material. For example, the stiffening element can include an electroactive polymer, a magnetoactive polymer, an ionic composite polymer, an electrorheological fluid, magnetorheological fluid, or a shape memory alloy. For example, an electroactive polymer stiffening element can include one or more dielectric electroactive polymer such as one or more ferroelectric polymers (e.g., copolymers comprising polyvinylidene difluoride ("PVDF")), dielectric elastomers, electrostrictive graft elastomers, or liquid crystalline polymers. For example, an electroactive polymer stiffening element can include one or more ionic electroactive polymer such as one or more conductive polymers, ionic polymer-metal composites (IPMCs), or responsive gels. For example, an electroactive stiffening element can include carbon structures (including nanostructures). For example, a magnetoactive polymer stiffening element can include a polymer with embedded magnetic or paramagnetic particles. For example, a stiffening element of a shape memory material can include a nickel-titanium shape memory alloy, such as nitinol or other suitable nickel-titanium alloy composition. In embodiments, the stiffening element 256 including at least one smart material or responsive material is responsive to an electric current, an electric field, or a magnetic field.

Figure 10A:
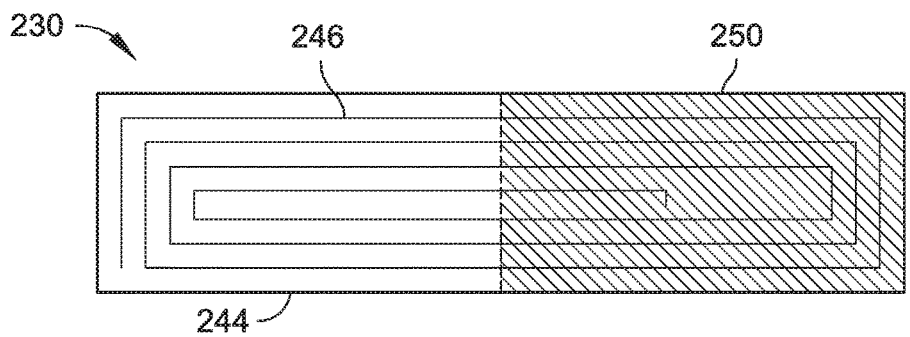
FIG. 10A is a schematic of an embodiment of an antenna assembly of an intraluminal device such as shown in FIG. 1.
Figure 10B:
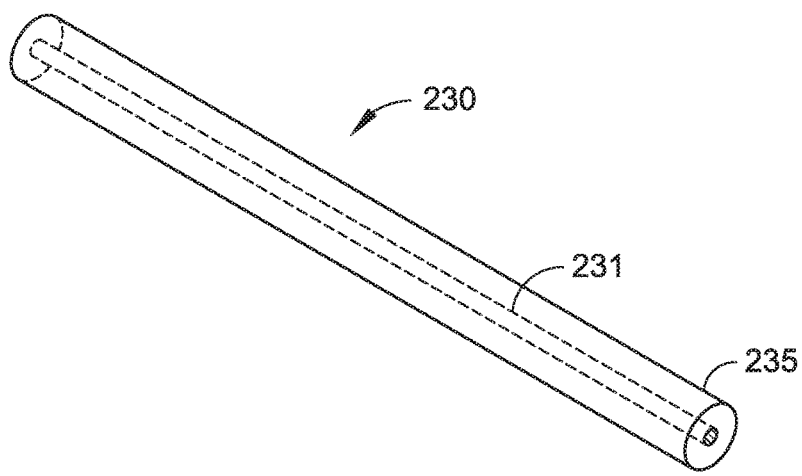
FIG. 10B is a schematic of an embodiment of an antenna assembly of an intraluminal device such as shown in FIG. 1.
Figure 10C:
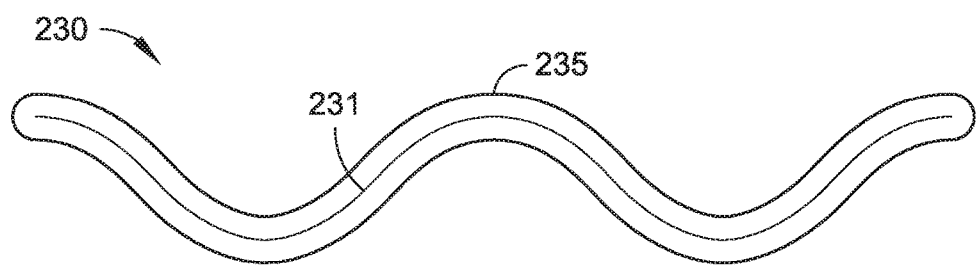
FIG. 10C is a schematic of an embodiment of an antenna assembly of an intraluminal device such as shown in FIG. 1.
Figure 10D:
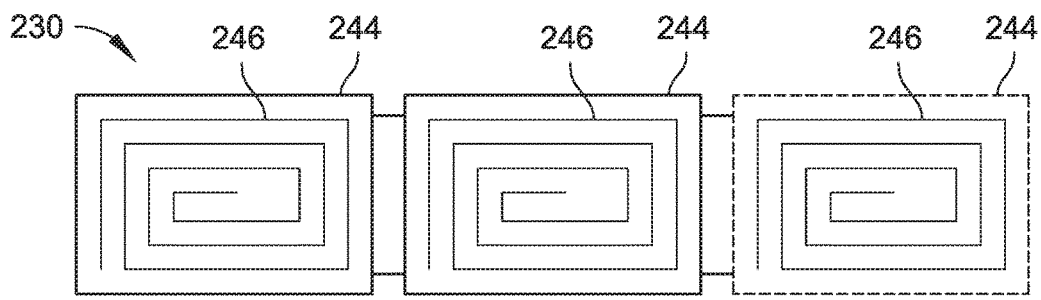
FIG. 10D is a schematic of an embodiment of an antenna assembly of an intraluminal device such as shown in FIG. 1.

FIGS. 10A through 10D show examples of the deployable element 104 configured as a deployable antenna assembly 230. For example, FIG. 10A shows an embodiment were the conductive layer 246 includes a conductive trace that defines at least one antenna (e.g., antenna 232) that is insulated by the flexible substrate 244 and the insulating layer 250. For illustrative purposes, the insulating layer 250 is shown in FIG. 10A as covering a portion of the conductive layer 246; however, the insulating layer 250 can fully cover the conductive layer 246 such that the conductive layer 246 is encapsulated between the substrate 244 and the insulating layer 250. The antenna 232 defined by the conductive layer 246 can be a loop antenna, a multi-turn loop antenna, a monopole antenna, a dipole antenna, a spiral antenna, a helical antenna, or the like. In embodiments, the antenna 232 can include a ferrite-loaded conductor (e.g., ferrite-loaded loop or coil defined by conductive layer or trace 246 or by a conductive wire or the like). In embodiments, the deployable element 104 defining the antenna assembly 230 can have a form factor other than a substantially flat sheet. For example, the deployable element 104 can include a tubular element (e.g., as shown in FIG. 10B) or a threadlike element (e.g., as shown in FIG. 10C), where the antenna assembly 230 includes a conductor 231 (e.g., a conductive wire) that defines the antenna element and an insulator 235 (e.g., a biocompatible nonconductive material) that substantially covers or coats the conductor 231. In embodiments, the deployable element 104 can include a plurality of sheet-like structures (e.g., as shown in FIG. 10D) or other segments that define separate antennas or portions of the same antenna. For example, the segments can unfold or telescope out to provide an antenna of extended length or a plurality of antennas that operate independent of one another or jointly (e.g., in series or in parallel) with one another. For example, FIG. 10D shows an embodiment where the antenna assembly 230 includes a plurality of substrates 244 having conductive layers 246 (e.g., traces) thereon. The conductive traces can be electrically connected with one another or each can have an independent electrical path (e.g., to a separate component of the intraluminal device 100).

In embodiments, the deployable antenna 230 assembly includes a first antenna 232 and at least a second antenna 234, and possibly a third, fourth, and so on. For example, the first antenna 232 can be electronically connected with a receiver 222, and the second antenna 234 can be electronically connected with a transmitter 226. In embodiments, one of the first antenna 232 or the second antenna 234 (or a third antenna 236) can be electronically connected with the inductive charging circuit 218. In embodiments, one of the first antenna 232 or the second antenna 234 (or a third antenna 236) can be electronically connected with the transceiver 238. In embodiments, the first antenna 232 is structured for transmitting or receiving frequencies within a first radio frequency band, and the second antenna 234 is structured for transmitting or receiving frequencies within a second radio frequency band that is different from the first radio frequency band. For example, the first antenna 232 may be structured for receiving frequencies for wireless power transfer, and the second antenna may be structured for transmitting or receiving frequencies for communication signals. In embodiments, the first antenna 232 is made from a different material (e.g., a differing conductive material) than that of the second antenna 234. In embodiments, the first antenna 232 comprises a different antenna configuration than that of the second antenna 234. For example, the first antenna 232 may be a a monopole antenna, and the second antenna 234 may be a dipole antenna, or any other combination of differing antenna configurations.

Figure 11A:
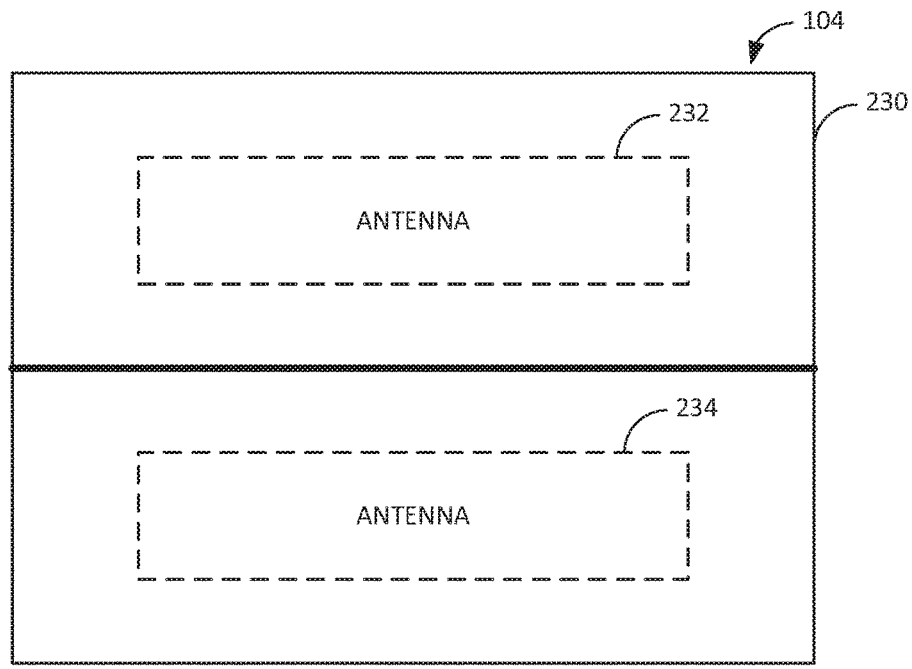
FIG. 11A is a schematic of an embodiment of an antenna assembly of an intraluminal device such as shown in FIG. 1.
Figure 11B:
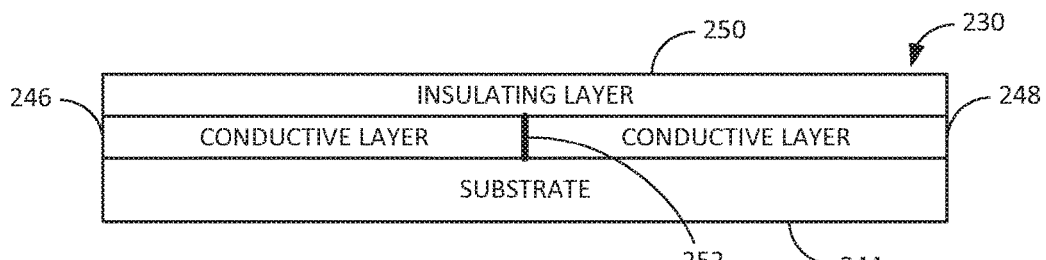
FIG. 11B is a schematic of an embodiment of an antenna assembly of an intraluminal device such as shown in FIG. 1.
Figure 12:
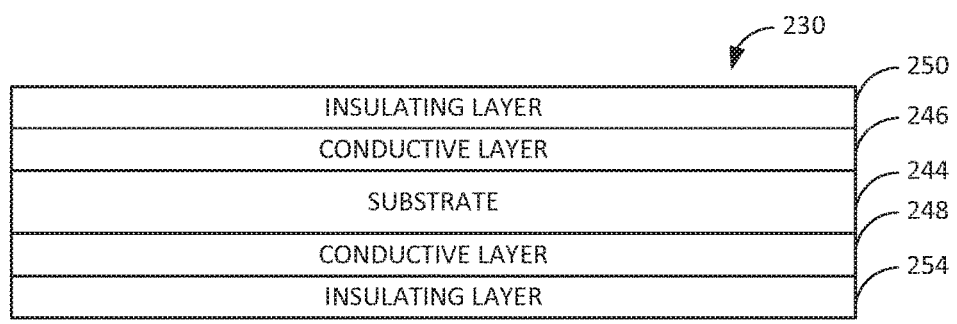
FIG. 12 is a schematic of an embodiment of an antenna assembly of an intraluminal device such as shown in FIG. 1.

The first antenna 232 is defined by a first insulated conductor and the second antenna 234 is defined by a second insulated conductor. As shown in FIGS. 11A and 11B, for example, the first antenna 232 can be defined by a first conductive layer or trace 246 on the substrate 244, and the second antenna 234 can be defined by a second conductive layer or trace 248 adjacent to the first conductive layer or trace 246, on the same substrate 244 or on an adjacent substrate. The first conductive layer or trace 246 and the second conductive layer or trace 246 can be insulated by the same insulating layer 250 or by adjacent insulating layers. In this manner, the one or more substrates 244 and the one or more insulating layers 250 can define separate chambers or compartments containing respective ones of the antennas 232 and 234. In embodiments, the first antenna 232 and the second antenna 234 can include insulated conductors that define tubular structures or threadlike structures. The antenna assembly 230 can also include a shielding element 252 (e.g., an RF shielding element) between the conductors (e.g. conductive layers or traces 246 and 248) that define antennas 232 and 234, respectively. In embodiments, the shielding element 252 includes at least one of a resonant structure, a grounded wire, a grounded trace, a grounded mesh, or the like. In embodiments, the first insulated conductor and the second insulated conductor include respective conductive layers or traces 246 and 248 disposed upon one side of the substrate 244 (e.g., as shown in FIG. 11B). In embodiments, such as the embodiment shown in FIG. 12, the first insulated conductor includes a first conductive layer or trace 246 disposed upon a first side of the substrate 244, and the second insulated conductor includes a second conductive layer or trace 248 disposed upon a second (e.g., opposite) side of the substrate 244, with respective insulating layers 250 and 254 for each side of the substrate 244.

As described herein and shown in FIG. 13, the second circuit portion 202 can include at least a portion of one or more antennas 232, sensors 210, therapeutic devices 212, or any combination thereof. For example, the conductive layer or trace 246 on the substrate 244 can define circuitry, device structure, or connectivity (e.g., one or more electrical pathways) for one or more of an antenna 232, sensor 210, or therapeutic device 212. In embodiments, the conductive layer or trace 246 defines pins for connecting to one or more antenna 232, sensor 210, or therapeutic device 212 components.

Figure 14:
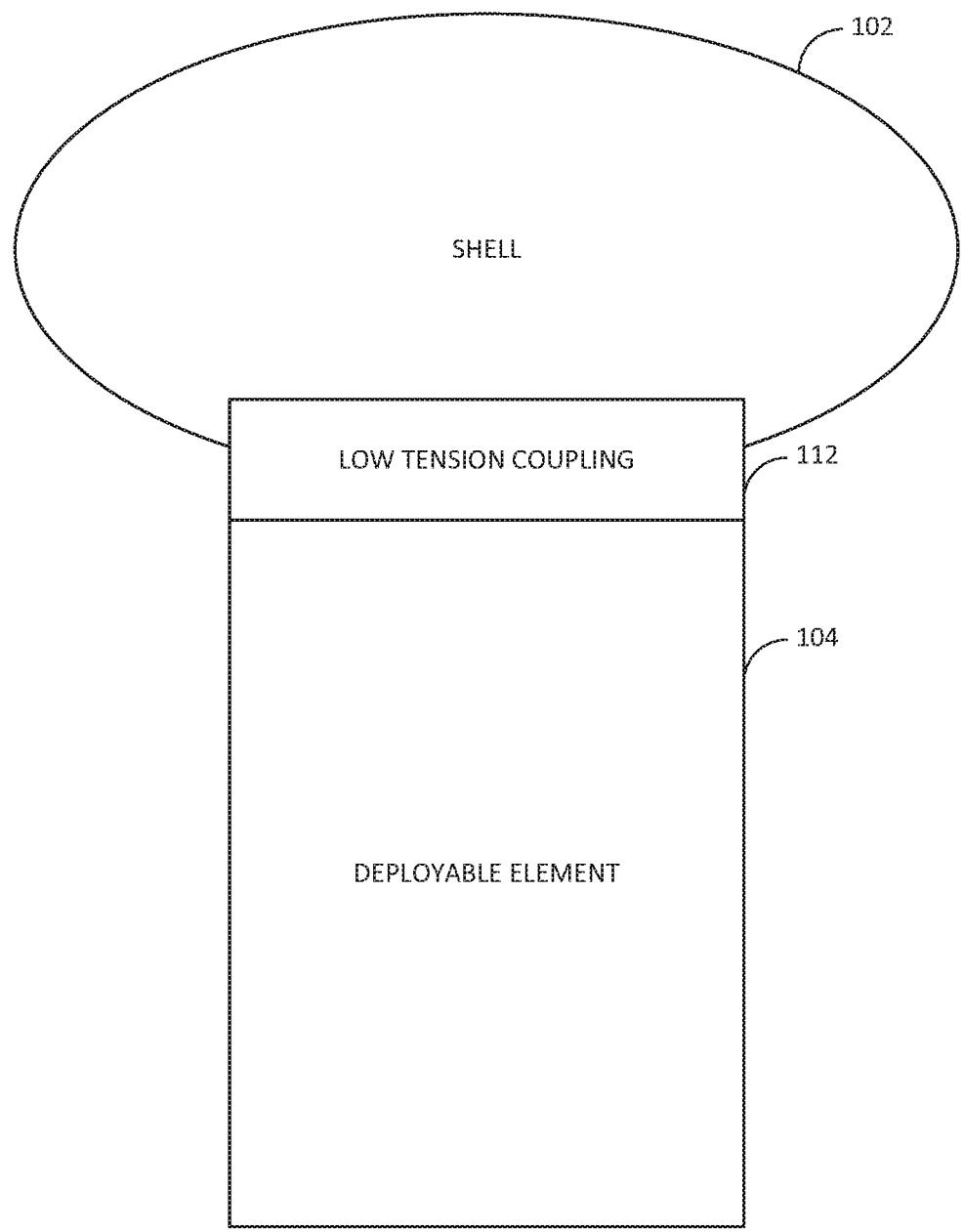
FIG. 14 is a schematic of an embodiment of an intraluminal device such as shown in FIG. 1.
Figure 15:
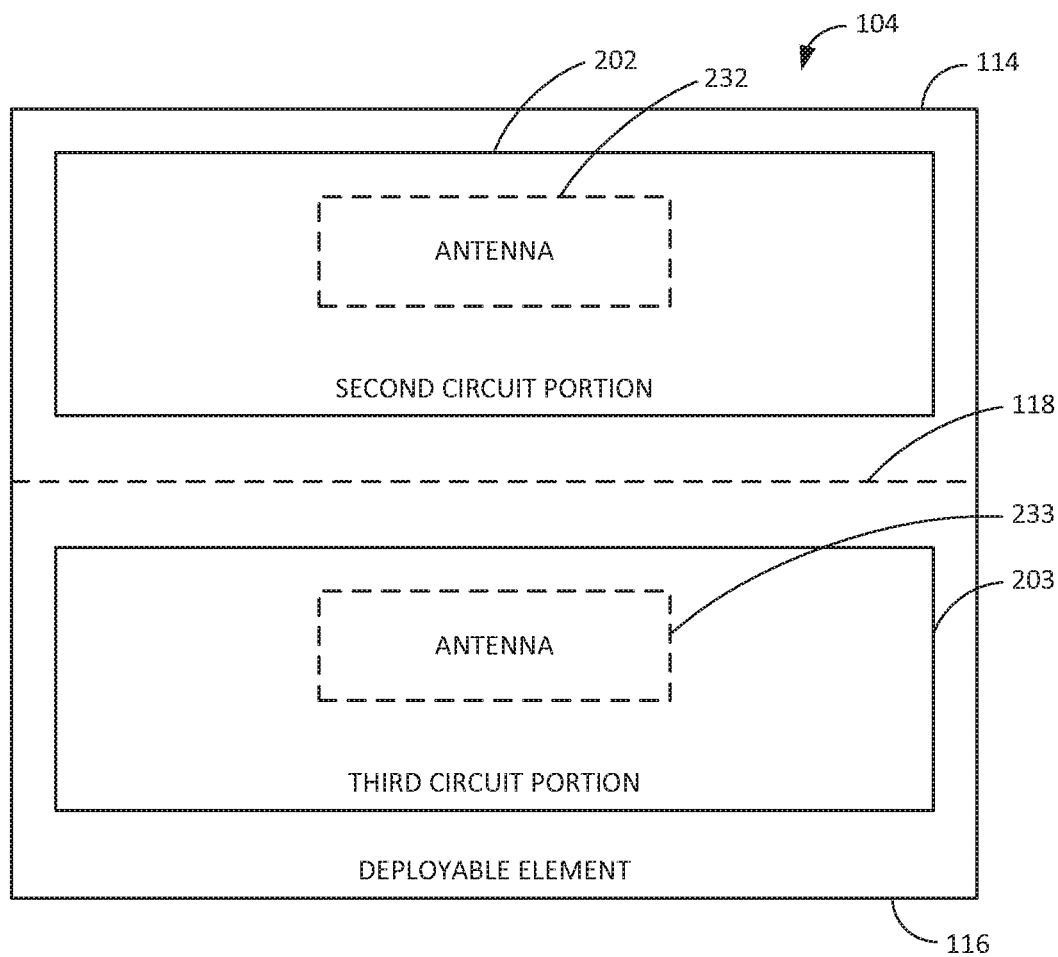
FIG. 15 is a schematic of an embodiment of a deployable element of an intraluminal device such as shown in FIG. 1.

FIGS. 14 and 15 show embodiments of the intraluminal device 100 including linkage structures for detaching at least a portion of the deployable element 104 under certain conditions. For example, FIG. 14 shows an embodiment where the deployable element 104 is coupled to at least one of the shell 102 or a component located within the shell 102 by a low tension coupling 112 (e.g., a perforated linkage, adhesive, quick release mechanical linkage, magnetic linkage, or the like) that disengages the deployable element 104 from the shell 102 or the component located within the shell 102 when a threshold value of tension occurs between the deployable element 104 and the shell 102 or the component located within the shell 102. In embodiments, (e.g., as shown in FIG. 15), the deployable element 104 includes a first assembly portion 114 and a second assembly portion 116 that are coupled by a low tension coupling (e.g., perforated portion of the flexible substrate 244 or other perforated linkage, adhesive, quick release mechanical linkage, magnetic linkage, or the like) that that disengages the first assembly portion 114 from the second assembly portion 116 when a threshold value of tension occurs between the first assembly portion 114 and the second assembly portion 116. In embodiments, the first assembly portion 114 can include the second circuit portion 202, and the third assembly portion 116 can include a third circuit portion 203 (which can be portion of the second circuit portion 202). The second circuit portion 202 may be operable independent of the third circuit portion 203 (e.g., operable even after the third circuit portion 203 is disengaged from the second circuit portion 202). For example, the second circuit portion 202 can include a first antenna 232 or antenna portion that is operable independent of a third antenna 233 or antenna portion located in the third circuit portion 203. In this manner the deployable element 104 or a portion thereof (e.g., assembly portion 116) can disengage from the remainder of the intraluminal device 100 if the deployable element 104 becomes stuck to a luminal wall or intraluminal structure.

Figure 17:
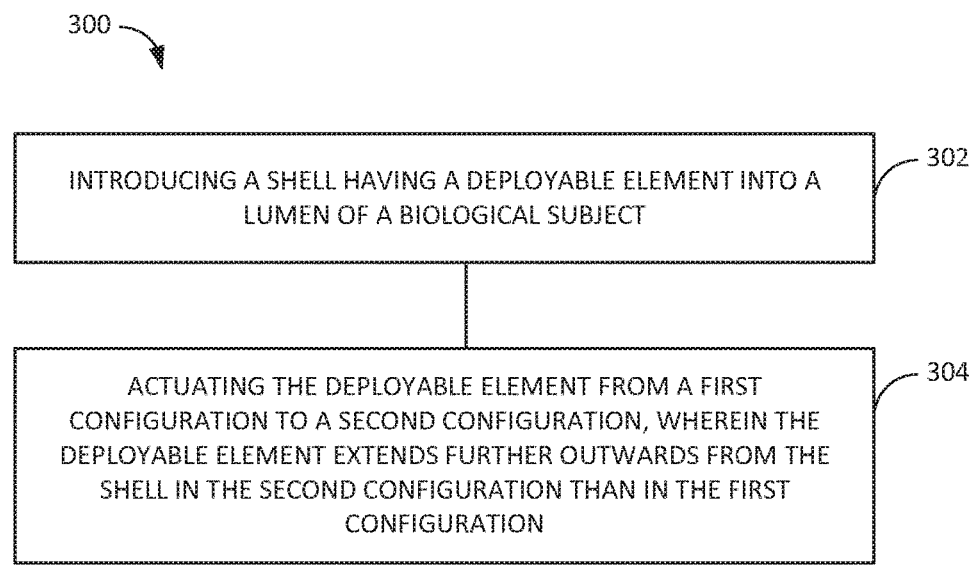
FIG. 17 is a flowchart of a method for controlling an intraluminal device, such as shown in FIG. 1, in accordance with an example embodiment.

FIG. 17 illustrates a method 300 for intraluminal analysis with an intraluminal device including a deployable element, such as the intraluminal device 100 according to various embodiments described herein. Method 300 shows introducing a shell with a deployable element attached to the shell into a lumen of a biological subject at block 302. For example, the shell 102 having the deployable element 104 attached to the shell in the first configuration (i.e., un-deployed) can be introduced to a biological lumen of a subject through one or more methods including, but not limited to, ingestion (e.g., for analysis of gastrointestinal systems), insertion, injection (e.g., for analysis of a respiratory system, a cardiovascular system, etc.), implanted delivery (e.g., a cut down procedure), via an endoscope, via a catheter, via a trocar, or the like. At block 304, the method 300 includes actuating the deployable element from a first configuration to a second configuration, wherein the deployable element extends further outwards from the shell in the second configuration than in the first configuration. For example, the actuator 242 can trigger the release mechanism 108 by causing the release mechanism to unlatch or unfasten in response to a mechanical or electromagnetic force applied by the actuator 242, thereby releasing the deployable element 104. In embodiments, the actuator 242 can directly actuate the deployable element 104 from the first configuration to the second configuration. For example, the actuator 242 can apply force to one or more portions of the deployable element 104. The actuator 242 can apply at least one of an electric current, an electric field, a magnetic field, fluid pressure, or mechanical spring force to actuate the deployable element 104 from the first configuration to the second configuration. In embodiments, the deployable element 104 is actuated from the first configuration to the second configuration when the biodegradable or dissolvable barrier 106 that at least partially covers or restrains the deployable element 104 is at least partially degraded or dissolved. The method 300 can further include at least one of: sending or receiving a wireless signal with an antenna included in the deployable element; sensing an intraluminal condition (e.g., temperature, pH, flow rate, intraluminal pressure, analyte concentration, or the like) with a sensor included in the deployable element; or performing a therapeutic or diagnostic activity with a therapeutic device included in the deployable element.

Figure 18:
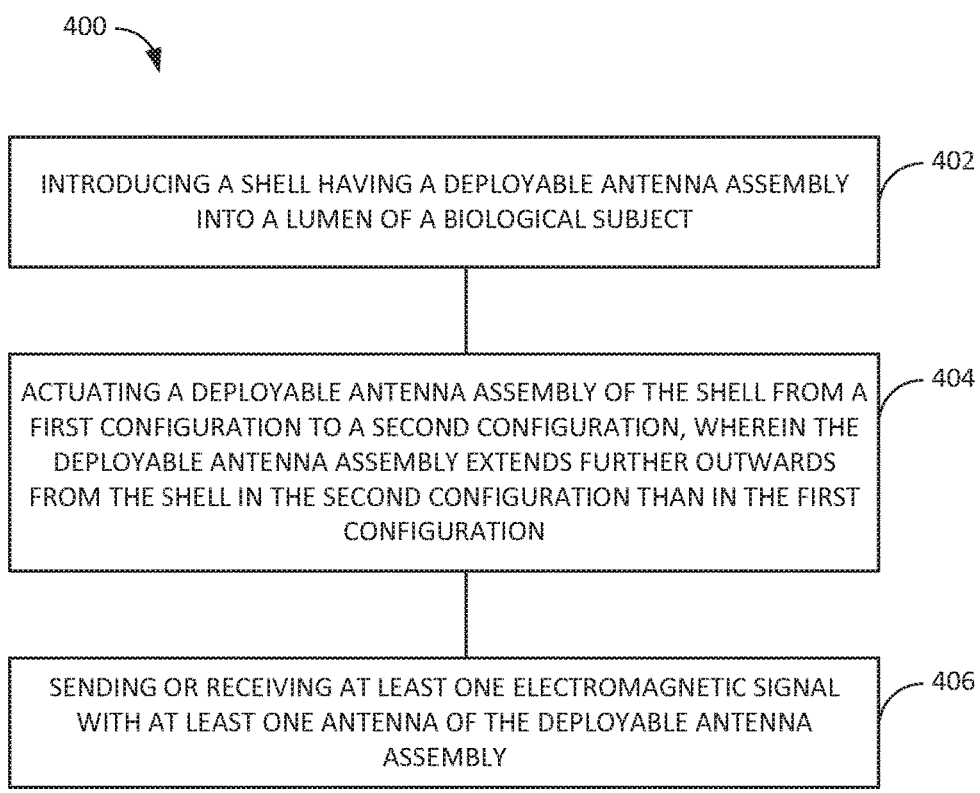
FIG. 18 is a flowchart of a method for controlling an intraluminal device, such as shown in FIG. 1, in accordance with an example embodiment.

FIG. 18 illustrates a method 400 for intraluminal analysis with an intraluminal device including a deployable antenna assembly, such as the intraluminal device 100 according to various embodiments described herein. Method 400 shows introducing a shell with a deployable antenna assembly attached to the shell into a lumen of the biological subject at block 402. For example, the shell 102 having the deployable antenna assembly 230 (e.g., incorporated in deployable element 104) in the first configuration (i.e., un-deployed) can be introduced to a biological lumen of a subject through one or more methods including, but not limited to, ingestion (e.g., for analysis of gastrointestinal systems), injection (e.g., by syringe, catheter, or endoscope for analysis of a respiratory system, a cardiovascular system, etc.), a cut down procedure, via an endoscope, via a catheter, via a trocar, or the like. At block 404, the method 400 includes actuating the deployable antenna assembly from a first configuration to a second configuration, wherein the deployable antenna assembly extends further outwards from the shell in the second configuration than in the first configuration. For example, the actuator 242 can trigger the release mechanism 108 by causing the release mechanism 108 to unlatch or unfasten in response to a mechanical or electromagnetic force applied by the actuator 242, thereby releasing the deployable element 104 having the antenna assembly 230 incorporated therein. In embodiments, the actuator 242 can directly actuate the deployable element 104 from the first configuration to the second configuration. For example, the actuator 242 can apply force to one or more portions of the deployable element 104. The actuator 242 can apply at least one of an electric current, an electric field, a magnetic field, fluid pressure, or mechanical spring force to actuate the deployable element 104 from the first configuration to the second configuration. In embodiments, the deployable element 104 is actuated from the first configuration to the second configuration when the biodegradable or dissolvable barrier 106 that at least partially covers or restrains the deployable element 104 is at least partially degraded or dissolved. At block 406, the method 400 includes sending or receiving at least one electromagnetic (e.g., RF signal) with at least one antenna of the deployable antenna assembly. For example, an antenna (e.g., antenna 232, 234, or 236) of the antenna assembly 230 can send or receive a communication (e.g., data) signal or can receive an electrical power signal for inductive charging from a source (e.g., computing device 122 or inductive charging coil 120) external to the lumen of the biological subject.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus.

In embodiments, the system is integrated in such a manner that the system operates as a unique system configured specifically for function of one or more of the systems described herein (e.g., intraluminal device 100) used to intraluminal devices with deployable elements having antenna, sensor, or therapeutic device components or circuitry incorporated therein, and any associated computing devices of the system operate as specific use computers for purposes of the claimed system, and not general use computers. In embodiments, at least one associated computing device of the system operates as a specific use computer for purposes of the claimed system, and not a general use computer. In embodiments, at least one of the associated computing devices of the system is hardwired with a specific ROM to instruct the at least one computing device. In embodiments, one of skill in the art recognizes that the systems described herein (e.g., intraluminal device 100) and associated systems/devices effect an improvement at least in the technological field of intraluminal devices with deployable elements.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. An intraluminal device, comprising:
a shell dimensioned and structured to travel through a biological lumen of a subject;
at least one of a sensor or a therapeutic device at least partially located within the shell;
at least one controller electronically connected with the at least one of the sensor or the therapeutic device;
at least one energy storage device;
at least one deployable antenna assembly including at least one antenna, the at least one antenna being electronically connected with at least one of the at least one controller or the at least one energy storage device, the at least one deployable antenna assembly being actuatable from a first configuration to at least a second configuration, wherein the first configuration includes the at least one antenna at least partially wrapped about an outer portion of the shell along a longitudinal axis of the shell, and wherein the at least one deployable antenna assembly extends further outwards from the shell in the second configuration than in the first configuration; and
an actuator for actuating the at least one deployable antenna assembly from the first configuration to the second configuration, wherein the at least one controller is electronically connected with the actuator and is configured to drive the actuator in response to at least one of a timer output, a sensor output, or a communication received from a source external to the biological lumen of the subject.

2. The intraluminal device of claim 1, further including:
at least one inductive charging circuit electronically connected between the at least one energy storage device and the at least one antenna, wherein the at least one antenna furnishes the at least one inductive charging circuit with energy received from at least one source external to the biological lumen of the subject.

3. The intraluminal device of claim 2, further including:
at least one impedance-matching circuit electronically connected between the at least one antenna and the at least one inductive charging circuit.

4. An intraluminal device, comprising:
a shell dimensioned and structured to travel through a biological lumen of a subject;
at least one of a sensor or a therapeutic device at least partially located within the shell;
at least one controller electronically connected with the at least one of the sensor or the therapeutic device;
at least one energy storage device; and
at least one deployable antenna assembly including at least one antenna including an insulated conductor, the insulated conductor including a conductive trace disposed upon a flexible substrate, wherein the flexible substrate includes pores, slits, or other openings to allow intraluminal fluid to flow therethrough, the at least one antenna being electronically connected with at least one of the at least one controller or the at least one energy storage device, the at least one deployable antenna assembly being actuatable from a first configuration to at least a second configuration, wherein the first configuration includes the at least one antenna at least partially wrapped about an outer portion of the shell along a longitudinal axis of the shell, and wherein the at least one deployable antenna assembly extends further outwards from the shell in the second configuration than in the first configuration.

5. The intraluminal device of claim 1, wherein the at least one deployable antenna assembly is coupled to at least one of the shell or a component located within the shell by a coupling that disengages the at least one deployable antenna assembly from the at least one of the shell or the component located within the shell when a threshold value of tension occurs between the at least one deployable antenna assembly and the at least one of the shell or the component located within the shell.

6. The intraluminal device of claim 1, further including:
at least one of a biodegradable barrier or a dissolvable barrier for maintaining the at least one deployable antenna assembly in the first configuration until the biodegradable barrier or the dissolvable barrier is at least partially degraded or dissolved.

7. The intraluminal device of claim 1, wherein the at least one of the sensor or the therapeutic device includes at least one of a temperature sensor, a pH sensor, a flow rate sensor, an intraluminal pressure sensor, an analyte sensor, an imaging device, an ultrasound transducer, an endoscopic surgical instrument, an endoscopic biopsy tool, an ablation tool, a radiation source, a syringe, a delivery tool, or a fluid pump.

8. An intraluminal device, comprising:
a shell dimensioned and structured to travel through a biological lumen of a subject; and
at least one deployable element, the at least one deployable element being actuatable from a first configuration to at least a second configuration, wherein the at least one deployable element extends further outwards from the shell in the second configuration than in the first configuration, and wherein the at least one deployable element is coupled to at least one of the shell or a component located within the shell by a coupling that detaches the at least one deployable element from the at least one of the shell or the component located within the shell when a threshold value of tension occurs between the at least one deployable element and the at least one of the shell or the component located within the shell, wherein the coupling includes a perforated linkage.

9. The intraluminal device of claim 8, wherein the at least one deployable element includes at least a portion of at least one of an antenna, a sensor, or a therapeutic device.

10. The intraluminal device of claim 8, wherein the at least one deployable element defines at least one of a substantially flat sheet-like structure, a tubular structure, or a flexible threadlike structure.

11. The intraluminal device of claim 10, wherein the at least one deployable element includes pores, slits, or other openings to allow intraluminal fluid to flow therethrough.

12. The intraluminal device of claim 8, further including:
an actuator for actuating the at least one deployable element from the first configuration to the second configuration.

13. The intraluminal device of claim 8, further including:
at least one of a biodegradable barrier or a dissolvable barrier for maintaining the at least one deployable element in the first configuration until the biodegradable barrier or the dissolvable barrier is at least partially degraded or dissolved.

14. An intraluminal device, comprising:
a shell dimensioned and structured to travel through a biological lumen of a subject;
at least one deployable element, the at least one deployable element being actuatable from a first configuration to at least a second configuration, wherein the at least one deployable element extends further outwards from the shell in the second configuration than in the first configuration;
an actuator for actuating the at least one deployable element from the first configuration to the second configuration responsive to control by a controller coupled to the shell in response to at least one of a timer output, a sensor output, or a communication received from a source external to the biological lumen of the subject;
at least one first circuit portion at least partially located within the shell; and
at least one second circuit portion at least partially located on or within the at least one deployable element, wherein the at least one first circuit portion is electronically connected with the at least one second circuit portion.

15. The intraluminal device of claim 1, wherein the at least one deployable antenna assembly at least partially extends radially outwards from the shell in the second configuration.

\* \* \* \* \*